United States Patent
Seppi et al.

(10) Patent No.: US 8,194,821 B2
(45) Date of Patent: Jun. 5, 2012

(54) METHODS, SYSTEMS, AND COMPUTER-PROGRAM PRODUCTS TO CORRECT DEGRADATION IN TOMOGRAPHIC IMAGES CAUSED BY EXTRANEOUS RADIATION

(75) Inventors: Edward Seppi, Portola Valley, CA (US); Edward Shapiro, Menlo Park, CA (US); Gary Virshup, Cupertino, CA (US); Josh Star-Lack, Palo Alto, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 12/239,699

(22) Filed: Sep. 26, 2008

(65) Prior Publication Data

US 2010/0080337 A1    Apr. 1, 2010

(51) Int. Cl.
*G01N 23/04* (2006.01)
(52) U.S. Cl. .............................. 378/62; 378/2
(58) Field of Classification Search .................. 378/62, 378/5, 156, 16, 2, 145, 108
See application file for complete search history.

(56) References Cited

U.S. PATENT DOCUMENTS

| | | | | |
|---|---|---|---|---|
| 3,974,386 | A * | 8/1976 | Mistretta et al. | 378/98.11 |
| 5,812,629 | A * | 9/1998 | Clauser | 378/62 |
| 6,633,627 | B2 * | 10/2003 | Horiuchi | 378/156 |
| 2004/0081280 | A1 * | 4/2004 | Avinash | 378/98.9 |
| 2004/0264755 | A1 * | 12/2004 | Sakaida | 382/128 |
| 2006/0062353 | A1 * | 3/2006 | Yatsenko et al. | 378/156 |
| 2006/0227933 | A1 * | 10/2006 | Cantu et al. | 378/62 |

* cited by examiner

*Primary Examiner* — Hoon Song
(74) *Attorney, Agent, or Firm* — Kilpatrick Townsend & Stockton LLP

(57) ABSTRACT

Disclosed are systems, methods, and computer program products that generate estimates of errors caused by extraneous radiation in tomographic systems, such as cone-beam computerized tomography (CBCT) systems, fluoroscopic tomography systems, radiographic tomography systems, laminar tomography imaging systems, and the like. In one group of inventions, spatial errors are estimated from projection data collected where a known spatial perturbation has been introduced into radiation intensity of the source. In another group of inventions, temporal errors are estimated from a sequence of projections where a known perturbation in the radiation intensity of the source for different projections has been introduced.

14 Claims, 9 Drawing Sheets

FIG. 1 *(PRIOR ART)*

Instruction Set #1 directs the data processor to obtain a first radiographic projection of an object, the first projection having a first portion generated from incident radiation having a first magnitude, a second portion generated from incident radiation having a second magnitude that is different from the first magnitude, and ratio T of the second magnitude to the first magnitude.

Instruction Set #2 directs the data processor to generate an estimate of a spatial error for a first area of the first projection, the first area being located in one of the first and second portions or located between the first and second portions, the first correction factor being generated from at least a projection value in the first portion, a projection value in the second portion, and the ratio T.

Instruction Set #3 directs the data processor to store the estimate in a computer-readable medium.

Instruction Set #4 directs the data processor to generate a corrected radiographic projection in relation to a difference of the first radiographic projection and the estimate of the spatial error.

COMPUTER-READABLE MEDIUM

FIG. 11

Instruction Set #1 directs the data processor to obtain a first radiographic projection of an object and a second radiographic projection of the object, the first projection having first and second portions generated from source radiation having a first magnitude $I1$ and the second projection having first and second portions generated from source radiation having a second magnitude $I2$, the second magnitude being different from the first magnitude.

Instruction Set #2 directs the data processor to generate an estimate of a spatial error for an area located in the first second radiographic projection, the area being located in one of the first and second portions of the first projection or located between the first and second portions, the estimate being generated from at least a projection value in the first portion of the first radiographic projection, a projection value in the second portion of the first radiographic projection, and a ratio T based on the properties of a spatial modulator interposed between the radiation source and the object.

Instruction Set #3 directs the data processor to generate an estimate of a temporal error for an area located in the first portion of the first or second radiographic projections or located in a first portion of an imaginary radiographic projection disposed in time between the first and second radiographic projections, the estimate being generated from at least a projection value in the first or second portions of the first radiographic projection, a projection value in the first or second portions of the second radiographic projection, and the first and second magnitudes $(I1, I2)$.

Instruction Set #4 directs the data processor to store the estimate in a computer-readable medium.

Instruction Set #5 directs the data processor to generate a corrected radiographic projection in relation to the first radiographic projection and the error estimates.

COMPUTER-READABLE MEDIUM

FIG. 12

METHODS, SYSTEMS, AND COMPUTER-PROGRAM PRODUCTS TO CORRECT DEGRADATION IN TOMOGRAPHIC IMAGES CAUSED BY EXTRANEOUS RADIATION

CROSS-REFERENCES TO RELATED APPLICATIONS

NOT APPLICABLE

BACKGROUND OF THE INVENTION

The present invention relates to tomography, and more particularly to correcting errors caused by extraneous radiation in tomographic systems, such as cone-beam computerized tomography (CBCT) systems, fluoroscopic tomography systems, radiographic tomography systems, laminar tomography imaging systems, and the like.

Computerized tomography (CT) involves the imaging of the internal structure of an object by collecting several projection images ("radiographic projections") in a single scan operation ("scan"), and is widely used in the medical field to view the internal structure of selected portions of the human body. Typically, several two-dimensional projections are made of the object, and a three-dimensional representation of the object is constructed from the projections using various tomographic reconstruction methods. From the three-dimensional image, conventional CT slices through the object can be generated. The two-dimensional projections are typically created by transmitting radiation from a "point source" through the object, which will absorb some of the radiation based on its size, density, and atomic composition, and collecting the non-absorbed radiation onto a two-dimensional imaging device, or imager, which comprises an array of pixel detectors (simply called "pixels"). Such a system is shown in FIG. 1. Typically, the point source and the center of the two-dimensional imager lie on a common axis, which may be called the projection axis. The source's radiation emanates toward the imaging device in a volume of space defined by a right-circular, elliptical, or rectangular cone having its vertex at the point source and its base at the imaging device. For this reason, the radiation is often called cone-beam (CB) radiation. Generally, when no object is present within the cone, the distribution of radiation is substantially uniform on any circular area on the imager that is centered about the projection axis, and that is within the cone. However, the distribution of the radiation may be slightly non-uniform, but having rotational symmetry about the projection axis. In any event, any non-uniformity in the distribution can be measured in a calibration step and accounted for. The projection axis may not be at the center of the imager or the center of the object. It may pass through them at arbitrary locations including very near the edge.

In an ideal imaging system, rays of radiation travel along respective straight-line transmission paths from the source, through the object, and then to respective pixel detectors without generating scattered rays. However, in real systems, when a quantum of radiation is absorbed by a portion of the object, one or more scattered rays are often generated that deviate from the transmission path of the incident radiation. These scattered rays are often received by "surrounding" pixel detectors that are not located on the transmission path that the initial quantum of radiation was transmitted on, thereby creating errors in the electrical signals of the surrounding pixel detectors. In addition, background radiation from the environment is often present, which can be a function of time and the position of the two-dimensional imager, which is often rotated about the object during a scan. The source of the radiation is typically not a point but has some size. The effect of this is often characterized by a source distribution function. Rays from outside some area, usually a circle, of the source distribution function create spatial error which is not accounted for using typical data analysis techniques. Furthermore, in typical two-dimensional imagers, the radiation meant to be received by a pixel is often distributed by various components of the imager (e.g., scintillation plate), and received by surrounding pixels. Also, there is typically some electrical cross-talk in the electrical signals of the pixel detectors caused by the electrical circuitry that reads the array of pixel detectors. These two effects are often characterized by a point-spread function (PSF), which is a two-dimensional mapping of the amount of error caused in surrounding pixels by a given amount of radiation received by a central pixel. The surface of the PSF is similar to the flared shape of a trumpet output, with the greatest amount of error occurring in pixels adjacent to the central pixel. Each of these non-ideal effects creates spatial errors in the pixel data generated by the two-dimensional imager.

Also in an ideal radiation imaging system, each pixel detector outputs an electrical signal that is representative of the radiation that strikes its designated area on the imager, and that responds instantaneously to changes in received radiation without any lagging or memory effects. However, pixel arrays, which are typically constructed with a scintillation plate disposed over an array of semiconductor diodes, have a number of lagging effects (also called memory effects). The scintillation plate, which converts the radiation into light that can be readily detected by the semiconductor diodes, has a finite conversion-delay time where the plate's scintillation material continues to luminesce for a period of time after being struck by a quantum of radiation. Each semiconductor diode, which typically comprises amorphous silicon, generates pairs of free electrons and free holes in response to light received from the portion of the scintillation plate above it, which then produce an electrical signal as they travel to respective electrodes of the diode. However, semiconductor materials, particularly amorphous ones, have carrier traps that capture and hold free electrons and free holes in the semiconductor material for varying periods of time before releasing them. When so trapped, a carrier generated by the scintillation light does not generate a corresponding electrical current at the time it was generated, but rather generates an electrical current sometime afterwards, thereby causing a lag effect. The trapping of carriers also causes changes in signal detection gain and signal offset of the diode. Each of these non-ideal effects creates temporal errors in the pixel data generated by the two-dimensional imager.

As part of making their inventions, the inventors have found that the spatial errors and the temporal errors cause artifacts (e.g., phantom images) and loss of resolution and contrast in the CT image slices produced by the radiation imaging system. They have also found that these errors cause numerical errors in the image reconstruction algorithms (generally referred to as "CT number problems" in the art). All of the foregoing lead to image degradation. While some of the specific effects that give rise to the above-described spatial and temporal errors have been given, it may be appreciated that other effects may exist. Nonetheless, the present inventions also address the errors that arise from such other effects. As a general summary, spatial errors at a given pixel detector are caused by radiation that does not travel along the direct path from the radiation source to the pixel detector; these errors include radiation scattered by the object being imaged, radiation scattered by the components of the two-dimensional imager, and cross-talk in the electrical circuitry that reads the pixel array. Temporal errors are caused by radiation that was incident on the detector element prior to the current measurement, with the detection of the prior radiation being erroneously read in the current measurement because of delays in the scintillation material, semiconductor material, or other components. Accordingly, there is a need in the computerized tomography field to reduce the impacts of these spatial and temporal errors.

BRIEF SUMMARY OF THE INVENTION

Several inventions of the present application address the impacts of the above-identified spatial and temporal errors by estimating their values by novel techniques, and several other inventions of the present application providing novel methods and systems for generating radiographic projections from which the spatial and temporal errors may be estimated. The estimates may then be subtracted from the measured data, or subtracted out from quantities in the line integrals used by many CT reconstruction algorithms, or otherwise factored out of algorithms used in a CT reconstruction procedure.

BRIEF DESCRIPTION OF THE DRAWINGS

FIGS. 11-12 show exemplary computer program products according to inventions of the present application.

DETAILED DESCRIPTION OF THE INVENTION

Figure 1:
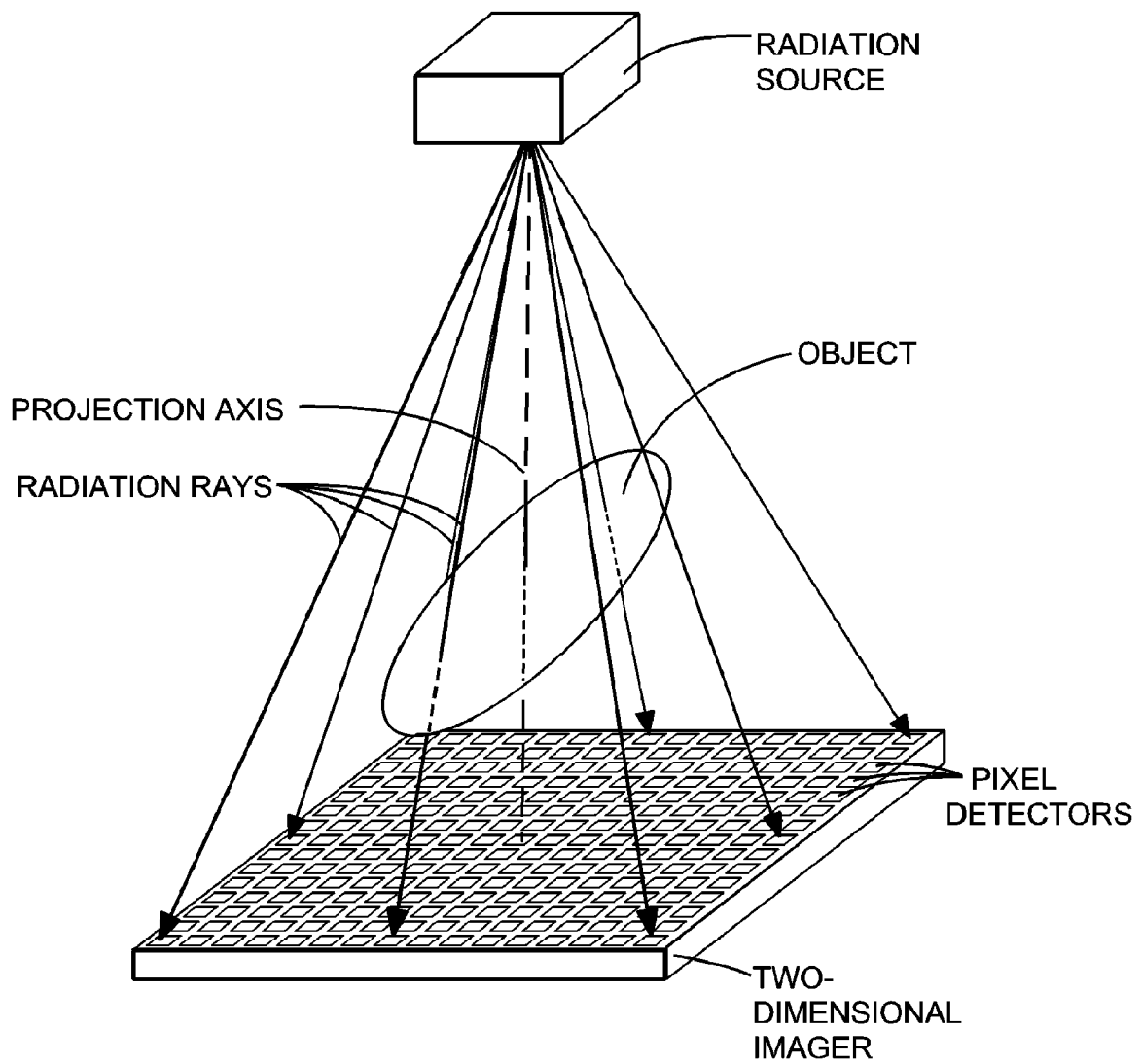
FIG. 1 is a schematic diagram of a radiation imaging system according to the prior art.

In the following description, numerous specific details are set forth to provide a more thorough description of specific embodiments of the present inventions. It is apparent, however, that the inventions may be practiced without all the specific details given below. In other instances, well known features have not been described in detail so as to not obscure the inventions. In addition, the following table of symbol nomenclature will provide a useful reference for the reader:

r—index for the projections;

x—a general x-coordinate designation for the two-dimensional imager in the X-domain;

y—a general y-coordinate designation for the two-dimensional imager in the Y-domain;

$(x_i, y_j)$—the x- and y-coordinates of a pixel of the two-dimensional imager at the i-th row and the j-th column;

$(X_m, Y_n)$—the x- and y-coordinates of a point of a coarse grid overlain on the area of the two-dimensional imager, the point being at the m-th row and the n-th column of the coarse grid;

$P_{TRUE}(x,y,r)$—the true image of the r-th projection at the x- and y-coordinates of the imager;

$P_{MEAS}(x,y,r)$—the measured data at the x- and y-coordinates of the imager with object (e.g., patient) in place; it includes the true image and extraneous data due to spatial effects and time-lag effects;

$P^M_{MEAS}(x,y,r)$—a spatially modulated version of the measured data $P_{MEAS}(x,y,r)$ of the imager with object (e.g., patient) in place, abbreviated as the spatially-modulated measured data $P^M_{MEAS}(x,y,r)$;

$E_{SPACE}(x,y,r)$—the space-domain error present within the spatially modulated version of the measured data ($P^M_{MEAS}$) caused by spatial effects;

$E_{TIME}(x,y,r)$—the time-domain error present within the measured data ($P_{MEAS}$) or spatially modulated version of the measured data ($P^M_{MEAS}$) caused by temporal effects;

Rep(x,y,r)—a representative value of the pixel values around a point (x,y) of the two-dimensional imager for a given projection r; the representative value will often be provided at a course grid point as $Rep(X_m, Y_n, r)$;

TP(x,y,r)—a transmission pattern function that relates $P^M_{MEAS}(x,y,r)$ to $P_{MEAS}(x,y,r)$ as $P^M_{MEAS}(x,y,r) = P_{MEAS}(x,y,r) \cdot TP(x,y,r)$; it can be measured empirically or computed based on the characteristics, dimensions, and placement of the spatial modulator; the value of TP(x,y,r) may depend on the path length through the object and thus may vary with the distance from the center of the spatial modulator; while written here as a function of r, is may be independent of r;

Gr(x,y,r)—the relative gain a detector or a group of detectors at a projection r relative to an initial value;

Z(x,y,r)—the ratio of Gr(x,y,r) at a projection r to the value of Gr(x,y,r−1) at the previous projection;

Og(x,y,r)—a time-dependent variation in the output of a detector or group of detectors at projection r;

$E'_{TIME}(x,y,r)$—the time-domain errors present within the measured data ($P_{MEAS}$) or spatially modulated version of the measured data ($P^M_{MEAS}$) caused by temporal effects, excluding the time-domain errors caused by changes in the relative gain of a detector or group of detectors;

ξ(x,y,3R)—a quantity used in approximating Z(x,y,3R) as 1+ξ(x,y,3R);

α(x,y,r)—an attenuation factor characterizing the actual or relative absorption of a material from which a spatial modulator is constructed;

Q(x,y,3R)—a ratio between two differences formed from three projection values.

Figure 2:
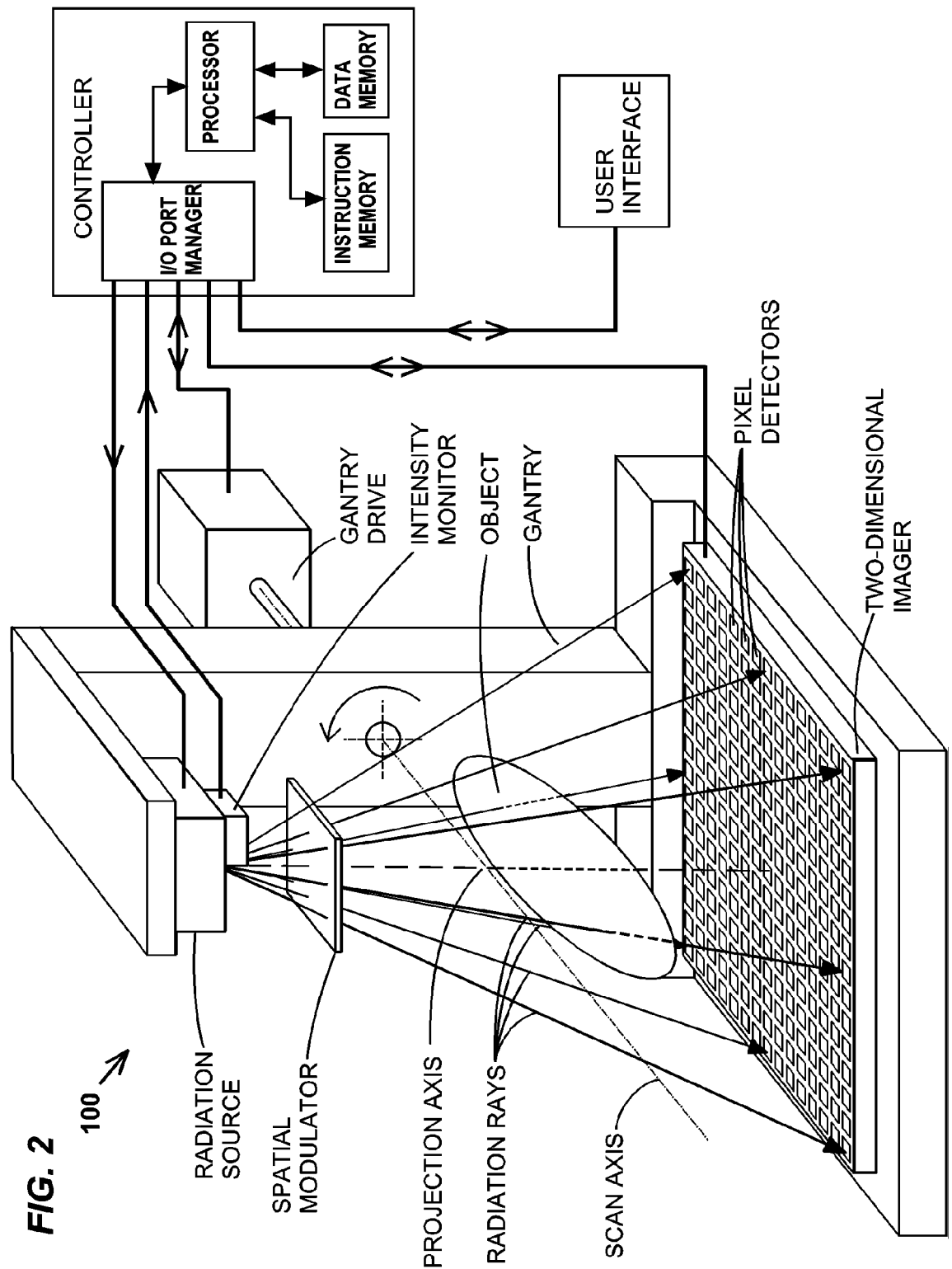
FIG. 2 is a schematic diagram of a first exemplary embodiment of a radiation imaging system according to the present invention.

FIG. 2 is a schematic diagram of an exemplary imaging system 100 according to the system inventions of the present application. System 100 comprises a radiation source, a two-dimensional imager disposed opposite to the radiation source along a projection axis, a spatial modulator disposed between the radiation source and the two-dimensional imager, a gantry that holds the radiation source and imager in a fixed spatial relationship, a gantry drive that rotates the gantry about an object disposed between the radiation source and the imager, a controller electrically coupled to the radiation source, the gantry drive, and the imager, and a user interface electrically coupled to the controller. For the sake of visual simplicity in the figure, the gantry housing, gantry support, and object support table are not shown. These components do not form part of the present inventions. The spatial modulator is located between the object to be imaged and the radiation source, and may be fixed to the radiation source or gantry housing (not shown) by any conventional support bracket or the like. As such, the spatial modulator is located closer to the radiation source than it is to the two-dimensional imager. The gantry is rotated about the object during a scan such that the radiation source and the two-dimensional imager circle around the object. More specifically, the gantry rotates the radiation source and the imager about a scan axis, as shown in the figure, where the scan axis is perpendicular to the projection axis. The gantry drive is mechanically coupled to the gantry to provide the rotation upon command by the controller. The user interface provides a human interface to the controller that enables the user to at least initiate a scan of the object, to collect measured projection data from the imager, and to collect estimates for the spatial errors and/or temporal errors. The user interface may be configured to present graphic representations of the measured data, estimates of the spatial errors and/or temporal errors, and the measured data as corrected by the removal of the estimates of the spatial errors and/or temporal errors.

The radiation that first strikes the object is termed herein as the "incident radiation." In one group of inventions of the application, as explained more fully below, spatial perturbations in the intensity of the incident radiation within each radiographic projection are introduced by the spatial modulator. In another group, temporal perturbations in the intensity of the incident radiation are introduced among the projections, such as by varying the power to the radiation source or by introducing a body of attenuation material between the source and the object for selected projections. In another group, both spatial and temporal perturbations are introduced.

There are two basic scan types: "full cone" and "partial cone." In a full cone scan, the projection axis is near the center of the imager, and some of the radiation rays pass on both sides of the object without hitting the object. In a partial cone scan, the projection axis is offset from the center of the imager in the transverse dimension near one edge of the imager, but approximately centered in the axial dimension; radiation rays clear the object on only one side. Other scan types exist, but these are two main ones. When the controller receives a request for a partial cone scan from the user to begin a scan of an object, the controller instructs the gantry drive to begin a 360-degree rotation of the gantry, and instructs the radiation source to begin emitting radiation. When the controller receives a request for a full cone scan from the user to begin a scan of an object, the controller instructs the gantry drive to begin a rotation of the gantry that is equal to 180 degrees plus the fan angle of the radiation cone, or a little bit more, and instructs the radiation source to begin emitting radiation. As it rotates, the gantry drive provides the controller with an indication of its angular displacement about the scan axis. The controller uses this information to read the values of the imager's pixel detectors as selected values of angular displacement to obtain the data for the radiographic projections. Typically, there are between 600 and 1000 projections taken in the 360 degrees or 180-degrees plus fan angle rotation, with each projection being spaced from adjacent projections by a set increment of angular displacement. The controller stores the data from each projection in a memory storage device, along with the angular displacement at which the projection was taken. The controller may also use the indication of angular displacement to instruct the radiation source to provide a selected radiation intensity for each projection. This provides for the temporal modulation in preferred embodiments of the invention. In one exemplary embodiment, the controller instructs the radiation source to alternate between two intensity values for the projections (e.g., odd-numbered projections receive a first intensity I1, and even-numbered projections receive a second intensity I2). In another exemplary embodiment, the controller instructs the radiation source to cycle through three intensity values among successive projections (e.g., I1, I2, I3, I1, I2, I3 . . . or I1, I2, I3, I2, I1, I2, I3, I2, I1 . . . ). The radiation source preferably includes an intensity monitor that generates an electrical signal representative of the intensity being output by the source for each projection. This signal is provided to the controller, which can use this signal to correct the measured pixel data for deviations in the source intensity with respect to the target intensity instructed by the controller. The electrical signal preferably has a lower degree of memory effects than that of the pixel detectors of the two-dimensional imager.

The controller comprises a processor, an instruction memory for storing instruction sets that direct the operation of the processor, a data memory that stores pixel and other data values used by the present inventions implemented by the imaging system, and an I/O port manager that provides input/output data exchange between the processor and each of the radiation source, the gantry drive, and the imager. The instruction memory, data memory, and I/O port manager are coupled to the main processor through a bidirectional bus structure. The instruction and data memory may be coupled to the processor through a dedicated memory bus, and may be implemented as different sections of the same memory device. The I/O port manager may use the same bus as used for the instruction and data memories. The operation of the processor is guided by a group of instruction sets stored in the instruction memory, which is an exemplary form of computer-readable medium. Exemplary instruction sets are illustrated below.

The controller comprises a processor, an instruction memory for storing instruction sets that direct the operation of the processor, a data memory that stores pixel and other data values used by the present inventions implemented by the imaging system, and an I/O port manager that provides input/output data exchange between the processor and each of the radiation source, the gantry drive, and the imager. The instruction memory, data memory, and I/O port manager are coupled to the main processor through a bidirectional bus structure. The instruction and data memory may be coupled to the processor through a dedicated memory bus, and may be implemented as different sections of the same memory device. The I/O port manager may use the same bus as used for the instruction and data memories. The operation of the processor is guided by a group of instruction sets stored in the instruction memory, which is an exemplary form of computer-readable medium. Exemplary instruction sets are illustrated below.

Figure 3:
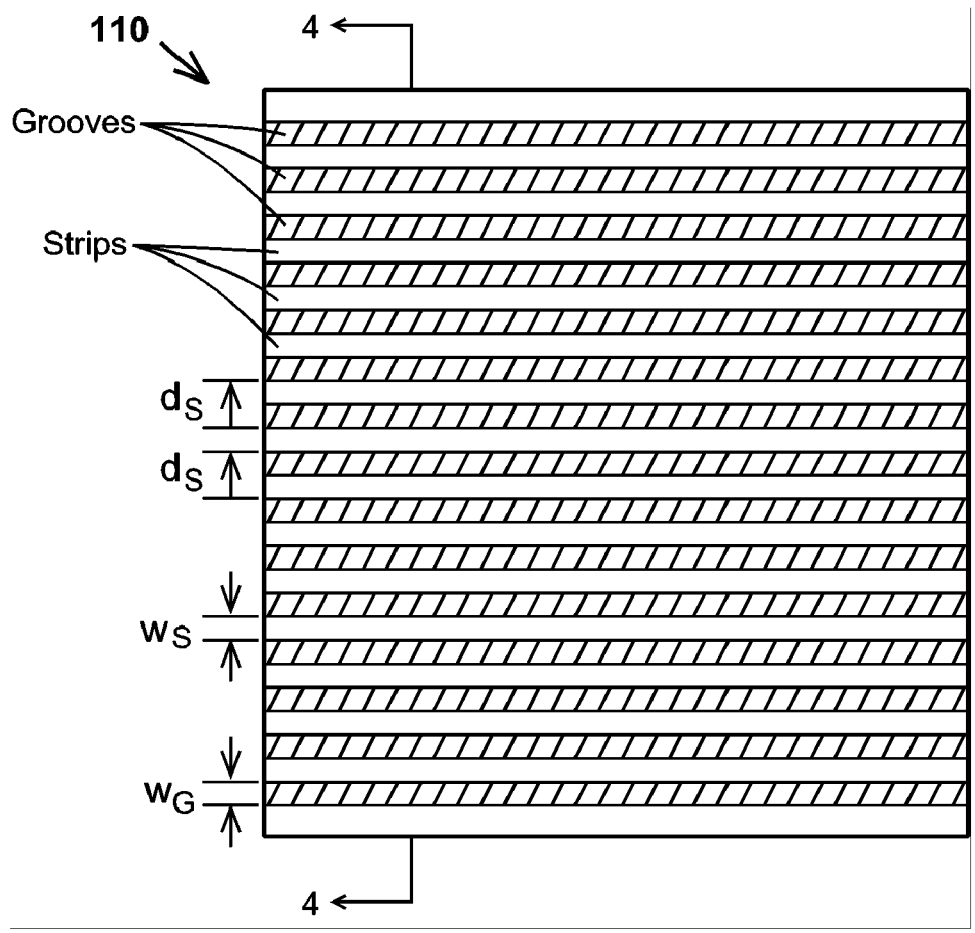
FIG. 3 is a top plan view of an exemplary spatial modulator according to inventions of the present application.
Figure 4:
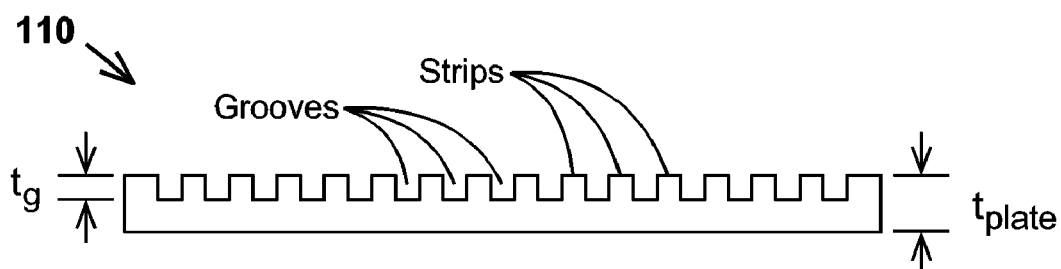
FIG. 4 is a side view of the exemplary spatial modulator shown in FIG. 3 according to inventions of the present application.

FIG. 3 shows a front plan view of an exemplary spatial modulator 110 used in some of the inventions of the present application, and FIG. 4 shows a side view of modulator 110. Exemplary modulator 110 comprises a plate of substantially rigid material with a plurality of grooves formed therein, preferably having smooth edges (e.g., smoothly changing).

The locations between grooves are referred to as strips. The strips are preferably equally spaced from one another by a distance $d_S$, with the grooves being equally spaced from one another by the same distance. The strips preferably have the same width $w_S$, and the grooves preferably have the same width $w_G$. Referring to FIG. 4, the plate preferably has a substantially uniform thickness $t_{plate}$, and the grooves preferably have the same depth $t_g$. Since radiation passing through the plate is attenuated in proportion to the amount of plate material it traverses, radiation passing through a strip is attenuated more than radiation passing through a groove. Thus, the radiation that reaches the object comprises a spatially modulated intensity pattern having a first set of parallel, spaced-apart, radiation bands of a first intensity, and a second set of parallel, spaced-apart, radiation bands of a second intensity interspersed between the first set of radiation bands. The radiation of the first set of bands passes through the grooves, and the radiation of the second set of bands passes through the strips. As such, the first intensity is greater than the second intensity. Because the radiation from the source is divergent (i.e., cone-beam), the dimensions of the radiation bands expand as the bands pass through the object and travel toward the two-dimensional imager. When they reach the imager, each band of the first set (which initially passed through a groove) has a width $W_G$, and each band of the second set (which initially passed through a strip) has a width $W_S$. Also, at the two-dimensional imager, each band is spaced from an adjacent band in its set by a distance $D_S$. The dimensions $W_G$, $W_S$, and $D_S$ are in proportion to the dimensions $w_G$, $w_S$, and $d_S$ of the plate, and follow the relationship: $W_G/w_G = W_S/w_S = D_S/d_S$. For a two-dimensional imager having x- and y-dimensions of 40 cm by 30 cm, plate 110 may comprise 30 grooves and 31 strips, with plate 110 oriented such that the length of the grooves run in the x-dimension of the imager. This configuration can be used to generate 30 bands having the first intensity and 30 bands having the second intensity on the imager, with $D_S = 1$ cm. With $w_G$ equal to $w_S$, each of $W_G$ and $W_S$ is equal to 0.5 cm. Plate 110 is preferably aligned to the two-dimensional imager such that the boundary between intensity bands falls between respective rows of pixel detectors, and is perpendicular to the projection axis (FIG. 2).

The plate's material preferably has an effective atomic (Z) number near that of the object being scanned so that the plate modulates the same radiation spectrum that the object absorbs, thereby minimizing any spectrum effects. Aluminum has an atomic (Z) number near that of tissue and is a suitable plate material to use for patients. Radiation passing through a strip is attenuated in proportion to the plate thickness $t_{plate}$, and radiation passing through a groove is attenuated in proportion to the quantity $(t_{plate} - t_g)$. The groove depth $t_g$ is selected such that the percentage difference between the intensities transmitted through a strip and those transmitted through a groove ranges from 3% to 15%, and typically ranges from 5% to 10%. A groove depth for any desired percentage difference can be estimated through conventional techniques for computing radiation absorption. In addition, test structures with varying groove depths can be constructed and their absorption characteristics measured in order to estimate a groove depth for a desired percentage difference. As an example, an aluminum plate having a thickness $t_{plate} = 4$ mm and a groove depth $t_g = 2$ mm provides a difference of 10%. We noted that, when using a flat plate spatial modulator 110, the source radiation passes through the spatial modulation at varying angles because of the cone-beam shape of the radiation. For example, the source radiation passes through the center of the flat plate at an angle of 90-degrees, and at angles of less than 90 degrees at other points, such as 75 degrees, with the lowest angles being at the corners and edges of the flat plate. As radiation passes through a lower angle, it sees an effective thickness that is greater than $t_{plate}$ (for strips) or $t_{plate} - t_g$ (for grooves), and undergoes more absorption. Accordingly, when using a flat plate, grooves at the plate edges will induce more absorption than grooves at the center, and the ends of the grooves will induce more absorption than the centers of the grooves. The same can be said for the strips. This spatial effect can be readily modeled and accounted for, either by modifying the design of the strips and grooves, or by deriving correction factors. Also, in an exemplary embodiment described below, the spatial variation in the absorption can be estimated and accounted for by using a spatial modulator that has regions of three different thicknesses distributed across the modulator, and by additional processing of the measure data. Finally, the spatial variation in absorption can be mitigated by using a plate that is shaped to follow the contour of a sphere having a radius equal to the distance between the radiation source and the plate; this construction enables the radiation to pass through the plate at an angle of substantially 90 degrees across the full extent of the plate.

Accordingly, it may be appreciated that a spatial modulator comprises a body of material, a plurality of first regions in the body of material that have thicknesses of the material that are equal to or less than a first thickness value, and a plurality of second regions in the body of material that have thicknesses of the material that are greater than the first thickness value. For the embodiment shown in FIG. 3, this first thickness value is equal to or greater than $(t_{plate} - t_g)$ and less than $t_{plate}$. Further, a plurality of the second regions are disposed along a geometry line with a plurality of first regions being disposed between these second regions (e.g., the first and second regions are disposed along a geometry line in an alternating manner). For a spatial modulator having regions of three different thicknesses (as described below in greater detail with respect to FIG. 9), the spatial modulator further comprises a plurality of third regions in the body of material that have thicknesses of the material that are equal to or greater than a second thickness value, wherein the second thickness value is greater than the first thickness value. In this spatial modulator, the thicknesses of the second locations are less than the second thickness value, and the three region types may be arranged in various alternating patterns along various geometry lines.

General Correction Framework. Each measured projection data, called $P_{MEAS}(x,y,r)$ herein, is modeled as comprising the true projection data, called $P_{TRUE}(x,y,r)$, plus errors caused by spatial effects (such as scattering and point spreading in the detector), and errors caused by temporal effects (such as various lagging effects of the detector). This is represented in general mathematical form as:

$$P_{MEAS}(x,y,r) = P_{TRUE}(x,y,r) + \text{Errors caused by spatial and temporal effects,} \qquad [0]$$

where (x.y) specifies a location on the two-dimensional imager, and r specifies the projection number. The true projection data $P_{TRUE}(x,y,r)$ will provide better image clarity and fewer artifacts in the images than the measured projection data $P_{MEAS}(x,y,r)$. However, the true projection data cannot be directly obtained from the imaging system, whereas the measured projection data $P_{MEAS}(x,y,r)$ can.

In a first set of inventions of the present application directed to estimating the error caused by spatial effects, a known spatial variation in the radiation incident upon the object is introduced during the measurement of $P_{MEAS}(x,y,r)$, which generates a spatially modulated version of the measured data.

The spatially modulated version is represented by the term $P^M_{MEAS}(x,y,r)$. The spatial variation can be readily provided by disposing a spatial modulator between the radiation source and the object (shown in FIG. 2), such as spatial modulator 110 shown in FIGS. 3 and 4. The spatial variation causes the projection seen by the two-dimensional imager to have a plurality of first portions (e.g., bands) whose pixel values are generated from incident radiation having a first magnitude, and a plurality of second portions (e.g., bands) whose pixel values are generated from incident radiation having a second magnitude that is different from the first magnitude, as described above with reference to FIGS. 3 and 4. In the case of using spatial modulator 110, the radiation rays passing through the plate in areas of the grooves are attenuated by a first amount, and propagate toward corresponding first portions of the two-dimensional imager, which take the form of a first set of parallel, spaced-apart radiation bands. Radiation rays passing through the plate in areas of the strips are attenuated by a second amount, and propagate toward corresponding second portions of the two-dimensional imager, which take the form of a second set of parallel bands that are interspersed between the first set of parallel bands. A transmission factor "T1" can be assigned to the rays passing through the grooves, and a transmission factor "T2" can be assigned to rays passing though the strips (i.e., the areas without grooves). Both transmission factors are less than 1. Based on the characteristics of the radiation, the material of the plate, and the thicknesses of the plate and grooves, the transmission factors T1 and T2 can be readily computed. They can also be empirically measured. Based on the factors T1 and T2, the geometry of the plate and its grooves, and the position of the plate relative to the radiation source and the two-dimensional imager, a transmission pattern function $TP(x,y)$ can be generated that relates $P_{MEAS}(x,y,r)$ and $P^M_{MEAS}(x,y,r)$ as follows:

$$P^M_{MEAS}(x,y,r) = P_{MEAS}(x,y,r) \cdot TP(x,y). \quad [1A]$$

This allows $P_{MEAS}(x,y,r)$ to be generated from $P^M_{MEAS}(x,y,r)$ as follows:

$$P_{MEAS}(x,y,r) = P^M_{MEAS}(x,y,r)/TP(x,y). \quad [1B]$$

$TP(x,y)$ can also be measured empirically, such as during a calibration procedure. The introduction of the spatial modulator does not, therefore, prevent $P_{MEAS}(x,y,r)$ from being obtained. In typical constructed embodiments, the ratio of T2/T1, also called the transmission ratio T, is in the range of ~0.85 to ~0.97, and more preferably in the range of ~0.90 to ~0.95.

With the spatial modulator in place, the true projection will be modulated by function $TP(x,y)$, and there will still be errors caused by spatial and temporal effects. Errors arising from spatial effects are called "space-domain errors" herein, and errors arising from temporal effects are called "time-domain errors." The space-domain errors may be represented as $E_{SPACE}(x,y,r)$, and the time-domain errors may be represented as $E_{TIME}(x,y,r)$. The modulated version $P^M_{MEAS}(x,y,r)$ can be approximately related to these quantities as follows:

$$P^M_{MEAS}(x,y,r) = TP(x,y) \cdot P_{TRUE}(x,y,r) + E_{SPACE}(x,y,r) + TP(x,y) \cdot E_{TIME}(x,y,r). \quad [2]$$

The space-domain error $E_{SPACE}(x,y,r)$ is not multiplied by the transmission pattern function $TP(x,y)$ in equation [2] because $E_{SPACE}(x,y,r)$ is the error that is to be determined with the spatial modulator in place. Note that $P_{TRUE}(x,y,r)$ is based on imager readings from radiation rays which are directed to pixel location $(x,y,r)$ on the imager, whereas $E_{SPACE}(x,y,r)$ is primarily the result of radiation rays which are not directed to pixel location $(x,y,r)$. More specifically, $E_{SPACE}(x,y,r)$ is the sum of scattered radiation caused by radiation rays that are not directed to pixel location $(x,y,r)$; in other words, spatial extraneous radiation. The major portion of the time-domain error $E_{TIME}(x,y,r)$ at a particular pixel arises from memory of readings from the direct rays to the pixel and scattered rays generated from rays passing through the same transmission band as the direct ray for projections prior to the current projection. For this reason, the time-domain error $E_{TIME}(x,y,r)$ has been modulated by the transmission pattern function $TP(x,y)$ in equation [2]. Some scattered rays received by a particular pixel are generated by other transmission bands having different transmission values, and the action of multiplying $E_{TIME}(x,y,r)$ by $TP(x,y)$ in equation [2] can lead to a small amount of over-estimation or under-estimation of the contribution of these scattered rays. However, it is believed that any underestimation or overestimation is a small secondary effect that does not significantly detract from the advantages and benefits of the present inventions. Known iterative procedures not discussed here can be used to reduce the magnitude of the secondary effects.

By sampling the measurement $^M_{MEAS}(x,y,r)$ on a coarse grid of points that are located where $TP=T2$, and then curve-fitting these sampled points to a first continuous projection surface $P_{T2}(x,y,r)$, the following projection surface can be obtained:

$$P_{T2}(x,y,r) = T2 \cdot P_{TRUE}(x,y,r) + E_{SPACE}(x,y,r) + T2 \cdot E_{TIME}(x,y,r). \quad [3]$$

The grid of points is relatively coarse, with the distance of two adjacent grid points spanning several pixels. In a similar manner, by sampling the measurement $P^M_{MEAS}(x,y,r)$ on another coarse grid of points that are located where $TP=T1$ and then curve-fitting these sampled points to another continuous projection surface $P_{T1}(x,y,r)$, the following projection surface can be obtained:

$$P_{T1}(x,y,r) = T1 \cdot P_{TRUE}(x,y,r) + E_{SPACE}(x,y,r) + T1 \cdot E_{TIME}(x,y,r). \quad [4]$$

The projection surfaces $P_{T1}(x,y,r)$ and $P_{T2}(x,y,r)$ are primarily introduced here to provide a theoretical framework for describing inventions of the present application, and do not have to be generated to practice the present inventions. As will be described below in exemplary embodiments, a representative value $Rep(X_m, Y_n, r)$ of the spatially-modulated measured data $P^M_{MEAS}(X_m, Y_n, r)$ around each coarse grid point $(X_m, Y_n)$ is preferably generated for the projection r, and these representative values may be used to approximate the projection surfaces $P_{T1}(x,y,r)$ and $P_{T2}(x,y,r)$. The generation of each representative value may include data smoothing (e.g., averaging) and data qualification of the pixel values in order to reduce the effects of random extraneous radiation. At any location $(x,y,r)$, equations [3] and [4] may be viewed as two linear equations in two unknowns: $E_{SPACE}(x,y,r)$ and the quantity $[P_{TRUE}(x,y,r) + E_{TIME}(x,y,r)]$, and the two linear equations can be solved for both of the unknowns. $E_{SPACE}(x,y,r)$ is slowly varying with respect to the coarse grids used to generate $P_{T1}(x,y,r)$ and $P_{T2}(x,y,r)$, whereas $P_{TRUE}(x,y,r)$ is generally not. Therefore, it is generally best to only use equations [3] and [4] to generate a good estimate of $E_{SPACE}(x,y,r)$, and to then subtract this estimate from both sides of equation [2] to generate an estimate of $TP(x,y) \cdot [P_{TRUE}(x,y,r) + E_{TIME}(x,y,r)]$.

More specifically, by multiplying equation [4] by $T=T2/T1$ and thereafter subtracting it from equation [3], the following relation may be obtained that removes $P_{TRUE}(x,y,r)$, and that substantially removes the time-domain error:

$$P_{T2}(x,y,r) - T \cdot P_{T1}(x,y,r) = (1-T) \cdot E_{SPACE}(x,y,r). \quad [5]$$

Equation [5] can be readily solved for $E_{SPACE}(x,y,r)$ as follows:

$$E_{SPACE}(x,y,r)=\{P_{T2}(x,y,r)-T \cdot P_{T1}(x,y,r)\}/(1-T). \quad [6]$$

$E_{SPACE}(x,y,r)$ may be subtracted from both sides of equation [2], and the resulting equation divided by $TP(x,y)$ to produce:

$$[P^M_{MEAS}(x,y,r)-E_{SPACE}(x,y,r)]/TP(x,y)=P_{TRUE}(x,y,r)+E_{TIME}(x,y,r). \quad [7]$$

Equation [7] gives the quantity $\{P_{TRUE}(x,y,r)+E_{TIME}(x,y,r)\}$ in terms of known values, and, if there is no temporal error, the value $P_{TRUE}(x,y,r)$. Exemplary embodiments described below show how approximations to the projection surfaces $P_{T1}(X_m,Y_n,r)$ and $P_{T2}(X_m,Y_n,r)$ can be generated at discrete grid points $(X_m,Y_n)$ from a set of representative values $Rep(X_m,Y_n,r)$, and then used to generate the space-domain error $E_{SPACE}(X_m,Y_n,r)$ at the discrete grid points $(X_m,Y_n)$. In fact, the projection surfaces $P_{T1}(X_m,Y_n,r)$ and $P_{T2}(X_m,Y_n,r)$ do not need to be generated to practice the present inventions since the space-domain error $E_{SPACE}(X_m,Y_n,r)$ can be generated directly from the representative values $Rep(X_m,Y_n,r)$ according to a number of mathematical forms, as described below. The value of the projection surfaces and equations [3]-[7] lies primarily in providing a framework from which the mathematical forms and their equivalents can be constructed. Applications of equations [6] and [7] work best when the values of T1 and T2 of $TP(x,y)$ are measured in a calibration step. A preferred calibration accounts for small variations away from the values of T1 and T2 present in $TP(x,y)$ caused by x-ray spectrum and path length differences through the object, and are included in the $TP(x,y)$ used in the solutions of equations [3] and [4]. Further below in this document, we describe exemplary embodiments that use a spatial modulator that has regions of three different thicknesses distributed across the modulator that provide three different transmission factors T1, T2, and T3. The use of three thicknesses, along with additional processing of the data, enables the values of $TP(x,y)$ to be effectively measured including the spectrum effects, and accounted for during a scan of an object. It obviates the need for a calibration step. This embodiment also estimates and accounts for the spatial variation in the absorption that can be caused by using a flat-plate spatial modulator.

A second set of inventions of the present application is directed to estimating the time-domain error $E_{TIME}(x,y,r)$, either alone or with the space-domain error $E_{SPACE}(x,y,r)$. In these embodiments, adjacent projections in a scan of an object are generated using different, but known, intensities of radiation, with the intensities used for adjacent projections typically being within 10% to 20% of one another. For each projection r there is a system (geometrical) configuration, for example a gantry angle. Better results are obtained if multiple projections are acquired at the same geometrical configuration and different intensities. This may multiply the number of projections for a scan, but the total dose can be held constant by appropriate reduction in radiation dose per projection. The time-domain error $E_{TIME}(x,y,r)$ is presumed to vary slowly enough so as to not be a function of the intensity changes; however, the attenuation of radiation through the object which gives rise to the true projection $P_{TRUE}(x,y,r)$ is a function of the intensity changes. Additionally, the space-domain error $E_{SPACE}(x,y,r)$ will also be a function of the intensity changes. Using the intensity-pattern function $IP(r)$ to represent a pattern of radiation intensities in the radiation source that varies from projection to projection, equation [2] may be generalized as:

$$P^M_{MEAS}(x,y,r)=IP(r) \cdot TP(x,y) \cdot P_{TRUE}(x,y,r)+IP(r) \cdot E_{SPACE}(x,y,r)+TP(x,y) \cdot E_{TIME}(x,y,r). \quad [8]$$

Without loss of generality, the example of intensity-pattern function $IP(r)$ alternating between two intensity values I1 and I2 is examined, with $IP(r)=I1$ for odd values of projections r, and $IP(r)=I2$ for even values of projections r. The odd projections will be denoted at ro, and the even projections will be denoted as re. This is a two-tier time-domain modulation that is similar to the two-tier modulation (T1,T2) produced by the space modulator. A three-tier time domain modulation, which has the ability to provide better corrections, is presented later.

By sampling the measurement $P^M_{MEAS}(x,y,ro)$ on a coarse grid of points that are located where $TP=T1$ and for odd-numbered projections $(IP(ro)=I1)$, and then curve-fitting (e.g., interpolating) these sampled points to a continuous projection surface as was done for equations [3] and [4], a projection surface $P_{I1,T1}(x,y,ro)$ based on equation [8] can be obtained for the odd projections ro:

$$P_{I1,T1}(x,y,ro,C1)=I1 \cdot T1 \cdot P_{TRUE}(x,y,ro,C1)+I1 \cdot E_{SPACE}(x,y,ro,C1)+T1 \cdot E_{TIME}(x,y,ro,C1), \quad [9A]$$

where the parameter C1 represents the system configuration for the particular value of ro, e.g., the projection angle of the projection. Similarly, by sampling the measurement $P^M_{MEAS}(x,y,ro)$ on a coarse grid of points that are located where $TP=T2$ and for odd-numbered projections $(IP(ro)=I1)$, and then curve-fitting (e.g., interpolating) these sampled points onto a continuous projection surface, another projection surface $P_{I1,T2}(x,y,ro)$ based on equation [8] can be obtained:

$$P_{I1,T2}(x,y,ro,C1)=I1 \cdot T2 \cdot P_{TRUE}(x,y,ro,C1)+I1 \cdot E_{SPACE}(x,y,ro,C1)+T2 \cdot E_{TIME}(x,y,ro,C1). \quad [9B]$$

Equations [9A] and [9B] may be viewed as two linear equations in the following two unknowns $E_{SPACE}(x,y,ro,C1)$ and $\{T1 \cdot P_{TRUE}(x,y,ro,C1)+E_{TIME}(x,y,ro,C1)\}$. They can be solved for $E_{SPACE}(x,y,ro,C1)$ in a manner similar to that used to obtain equation [6] from the equation pair equations [3] and [4]. This solution may be expressed as:

$$E_{SPACE}(x,y,ro,C1)=\{P_{I1,T2}(x,y,ro)-T \cdot P_{I1,T1}(x,y,ro)\}/(1-T), \quad [9C]$$

where $T=T2/T1$.

Similar projection surfaces can be obtained for the second intensity level I2 during the even-numbered projections. Specifically, by sampling the measurement $P^M_{MEAS}(x,y,re)$ on a coarse grid of points that are located where $TP=T1$ and for even-numbered projections $(IP(re)=I2)$, and then curve-fitting (e.g., interpolating) these sampled points onto the coarse grids, the following projection surface $P_{I2,T1}(x,y,re,C2)$ based on equation [8] can be obtained for the even projections re:

$$P_{I2,T1}(x,y,re,C2)=I2 \cdot T1 \cdot P_{TRUE}(x,y,re,C2)+I2 \cdot E_{SPACE}(x,y,re,C2)+T1 \cdot E_{TIME}(x,y,re,C2) \quad [10A]$$

where the parameter C2 represents the system configuration for the particular value of re, e.g., the projection angle of the projection. Similarly, by sampling the measurement $P^M_{MEAS}(x,y,ro)$ on a coarse grid of points that are located where $TP=T2$ and for even-numbered projections $(IP(re)=I2)$, and then curve-fitting (e.g., interpolating) these sampled points onto a continuous projection surface, the projection surface $P_{I2,T2}(x,y,re,C2)$ based on equation [8] can be obtained:

$$P_{I2,T2}(x,y,re,C2)=I2 \cdot T2 \cdot P_{TRUE}(x,y,re,C2)+I2 \cdot E_{SPACE}(x,y,re,C2)+T2 \cdot E_{TIME}(x,y,re,C2). \quad [10B]$$

Equations [10A] and [10B] may be viewed as two linear equations with the following two unknowns: $E_{SPACE}(x,y,re,C2)$ and $\{I2 \cdot P_{TRUE}(x,y,re,C2)+E_{TIME}(x,y,re,C2)\}$. They can be solved for $E_{SPACE}(x,y,re,C2)$ in a manner similar to that used for the equation pair equations [3] and [4]. This solution may be expressed as:

$$E_{SPACE}(x,y,re,C2)=\{P_{I2,T2}(x,y,re)-T\cdot P_{I2,T1}(x,y,re)\}/(1-T) \quad [10C]$$

where T=T2/T1.

For projection pairs re and ro where C1=C2, except for the presence of random and/or systematic errors, the values determined for $E_{SPACE}(x,y,re,C2)$ and $E_{SPACE}(x,y,ro,C1)$ are equal. Actions can be taken to reduce random and systematic errors, as described below. Because $E_{SPACE}(*)$ is slowly varying with respect to the parameters x, y, r, and C, $E_{SPACE}(x,y,re,C2)$ and $E_{SPACE}(x,y,ro,C1)$ should be very close in value for adjacent projections re and ro where C1 and C2 are only slightly different. Either of the values determined for $E_{SPACE}(*)$, or an average thereof, can be placed in equations [9A] and [10A], and the equations rearranged to obtain the following two liner equations for x-y locations where TP(x,y)=T1:

$$I1\cdot P_{TRUE}(x,y,ro,C1)+E_{TIME}(x,y,ro,C1)=\{P_{I1,T1}(x,y,ro,C1)-I1\cdot E_{SPACE}(x,y,r)\}/T1 \quad [11A]$$

$$I2\cdot P_{TRUE}(x,y,re,C2)+E_{TIME}(x,y,re,C2)=\{P_{I2,T1}(x,y,re,C2)-I2\cdot E_{SPACE}(x,y,r)\}/T1, \quad [11B]$$

where the unknown values appear in the left-hand sides of the equations and the known values appear in the right-hand sides. Because $E_{TIME}(*)$ is slowly varying with respect to the parameters x, y, r, and C, $E_{TIME}(x,y,ro,C1)$ and $E_{TIME}(x,y,re,C2)$ should be very close in value for adjacent projections re and ro where C1 and C2 are only slightly different. Also, since the projections $P_{I1,T1}(*)$ and $P_{I2,T1}(*)$ are generated from coarse grids, the variables $P_{TRUE}(*)$ in equations [11] will effectively be slowly varying. Thus, equations [11A] and [11B] have two unknowns $P_{TRUE}(x,y,r)$ and $E_{TIME}(x,y,r)$, which can be solved. In practice, the equations are only solved for $E_{TIME}(x,y,r)$. The solved values for $E_{SPACE}(x,y,r)$ and $E_{TIME}(x,y,r)$ are then used in Equation [8] to generate values for $P_{TRUE}(x,y,r)$ over the x- and y-domains for the adjacent projections ro and re. One way of solving equations [11A] and [11B] for $E_{TIME}(x,y,r)$ for the adjacent projections ro and re is provided below for x-y locations where TP(x,y)=T1:

$$E_{TIME}(x,y,r):=\{P_{I1,T1}(x,y,r)-(I1/I2)\cdot P_{I2,T1}(x,y,r)\}/\beta1 \quad [11C]$$

where $\beta1=(1-I1/I2)\cdot T1$. Of course, there are corresponding equations to equations [11A] and [11B] for pixel locations where TP(x,y)=T2, and these corresponding equations are functions of surfaces $P_{I1,T2}(x,y,ro,C1)$ and $P_{I2,T2}(x,y,re,C2)$. The corresponding equations may be readily obtained by substituting T2 for T1 in equations [11A] and [11B]. The corresponding equations may be solved for $E_{TIME}(x,y,r)$ for the adjacent projections ro and re, and the solution is provided below for x-y locations where TP(x,y)=T2:

$$E_{TIME}(x,y,r):=\{P_{I1,T2}(x,y,r)-(I1/I2)\cdot P_{I2,T2}(x,y,r)\}/\beta2 \quad [11D]$$

where $\beta2=(1-I1/I2)\cdot T2$. Equations [11C] and [11D] give estimates of $E_{TIME}(x,y,r)$ in terms of known values. Except for the presence of random and/or systematic errors, the estimates of $E_{TIME}(x,y,r)$ generated from equations [11C] and [11D] should be substantially close in value, and they may be averaged to provide a final estimate.

The above provides one approach for using equations [8]-[11] to generate estimates for $E_{SPACE}(x,y,r)$ and $E_{TIME}(x,y,r)$. For each configuration C1 and C2 that are equal or sufficiently close, the four equations [9A], [9B], [10A], and [10B] basically have three unknowns $P_{TRUE}(x,y,r)$, $E_{SPACE}(x,y,r)$, and $E_{TIME}(x,y,r)$. As such, the four equations mathematically over determine these unknown. According, another approach is to use any conventional least-squares mathematical method to find an optimum minimum root-mean-square (RMS) solution for the values of the three unknowns. The solved values for $E_{SPACE}(x,y,r)$ and $E_{TIME}(x,y,r)$ may then be used in equation [8] to generate values for $P_{TRUE}(x,y,r)$ over the imager's x-y domain for the adjacent projections ro and re, as described above. This approach can be further extended to include additional projection surfaces generated from additional transmission values, such as TP=T3, and additional irradiation values, such as IP=I3.

Figure 5:
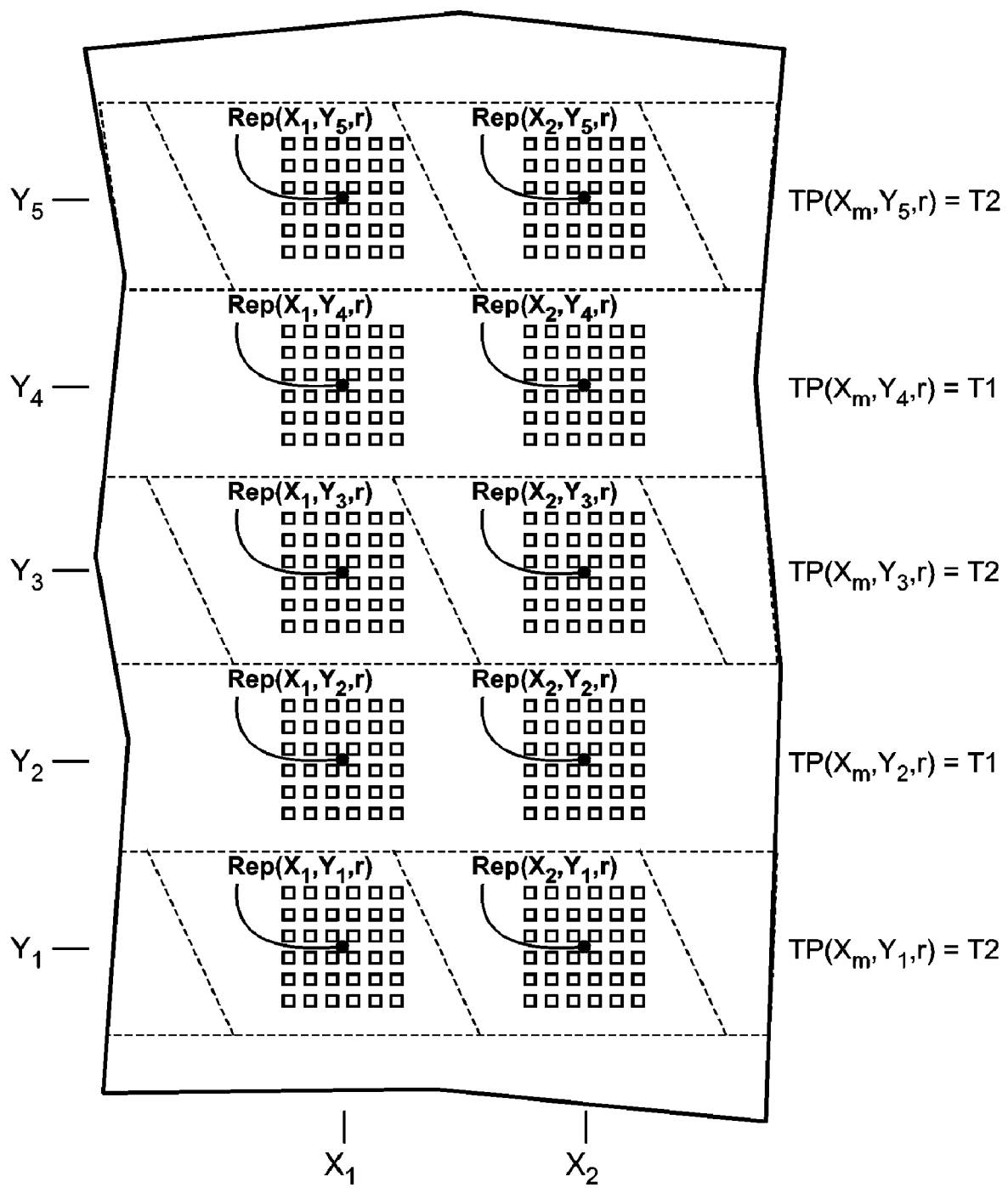
FIG. 5 shows a portion of a two-dimensional imager to illustrate an exemplary embodiment of an invention of the present application.

Embodiments of the present inventions are based from selected ones of the above equations, and the embodiments use representative values $Rep(X_m,Y_n,r)$ of the measured projection values $P^M{}_{MEAS}(X_m,Y_n,r)$ at points $(X_m,Y_n)$ of a coarse grid for a projection r, where the coordinates of the coarse grid are identified herein as $X_m$ with index m=1,2,3 . . . and $Y_n$ with index n=1,2,3, . . . . The embodiments then generate estimates for one or both of $E_{SPACE}(X_m,Y_n,r)$ and $E_{TIME}(X_m,Y_n,r)$ for the points $(X_m,Y_n)$ of the coarse grid, and then interpolate the estimates to all of the pixel locations $(x_i,y_j)$ to provide $E_{SPACE}(x_i,y_j,r)$ and $E_{TIME}(x_i,y_j,r)$. As an example, when using a spatial modulator 110 having 30 grooves with a two-dimensional imager having x-y dimensions of 40 cm by 30 cm and 1024 pixels by 768 pixels (pixel spacing of 0.388 mm), an $X_m$-$Y_n$ grid having 267 grid points in the $X_m$-dimension and 60 grid points in the $Y_n$-dimension (one per radiation band) can be used. The $X_m$-$Y_n$ grid points can be located at corresponding pixel locations or located between pixel locations. Once estimates for $E_{SPACE}(X_m,Y_n,r)$ and $E_{TIME}(X_m,Y_n,r)$ are generated at the $X_m$-$Y_n$ grid points, they can be generated for each pixel location $(x_i,y_j)$ by any conventional interpolation or extrapolation method to provide $E_{SPACE}(x_i,y_j,r)$ and $E_{TIME}(x_i,y_j,r)$. FIG. 5 shows a portion of the two-dimensional imager that includes ten grid points (shown as solid dots in the figure) at the $X_m$-coordinate locations of $X_1$ and $X_2$ and $Y_n$-coordinate locations $Y_1$, $Y_2$, $Y_3$, $Y_4$, and $Y_5$. The portion has three bands where the image is produced with the transmission function TP(x,y,r) equal to T2, which are interspersed between four bands where the image is produced with the transmission function TP(x,y,r) equal to T1. The portion of the imager has several hundred pixels, but only ten groups of 36 pixels each are shown for visual clarity. Each group of pixels preferably forms a 6-by-6 array that is substantially centered on a respective $X_m$-$Y_n$ grid point and associated therewith, with each array preferably being within a single band. In the example shown, each $X_m$-$Y_n$ grid point is disposed equidistant from four adjacent pixels at the center of the array since the array has an even number of pixels on each side. If an array having an odd number of pixels is used, such as 5-by-5, then each $X_m$-$Y_n$ grid point may be centered on a respective pixel. In order to clearly show the pixels in the figure, they have been enlarged relative to the width of the intensity bands in the figure, by approximately a factor of two for a typical implementation. The shape of the array need not be square, and may have any shape, including that of a rectangle, triangle, polygon, circle, oval, etc. Also, an array need not use all the pixels that fall within the grid area of the corresponding $X_m$-$Y_n$ grid point (the grid area is the area that encompasses pixels that are closer to the $X_m$-$Y_n$ grid point than other $X_m$$Y_n$ grid points).

For each projection r, the pixels of an array provide measured projection values $P^M{}_{MEAS}(x_i,y_j,r)$ around the associated $X_m$-$Y_n$ grid point, and these values have a numeric distribution. A representative value $Rep(X_m,Y_n,r)$ of the distribution may be generated for each associated $X_m$-$Y_n$ grid point, with the representative value $Rep(X_m,Y_n,r)$ being in the range from the highest value to the lowest value of the pixel values in the array. In preferred embodiments, a representative value is generated such that the distribution is substantially centered about the representative value, but this is not a necessary requirement of the present inventions. A representative value may be generated according to any known mathematical form for mean values, median values, mode values, percentile values, and the like, variants thereof, and combinations thereof. Common examples of mean values are: the conventional average value, a weighted average, a generalized mean, a geometric mean, a harmonic mean, etc., truncated versions thereof (e.g., where high and/or low values in the distribution are discarded), and variants thereof. A median value is any value that separates the highest half of the array pixel values from the lowest half, a truncated median value is a median value in which some of the pixel array values have been discarded before the median value is determined (such as the highest and/or lowest values). A mode value is a frequent or the most frequent pixel value or quantized pixel value in an array of pixel values (and a truncated version is one in which some of the pixel values have been discarded).

In preferred embodiments, a representative value is generated such that the corresponding distribution is substantially centered about the representative value. In one example, a representative value is generated by first computing an initial average of the pixel values in the array, then computing the root-mean-square (RMS) deviation of the values from the average. The pixel values are denoted herein as $pv_i$, $i=1, 2, \ldots N$, the initial average is denoted as $\overline{pv}$, the deviation of each pixel value from the average is $(pv_i - \overline{pv})$ $i=1, 2, \ldots N$, and the RMS deviation can be generated according to the following form:

$$\text{RMS Deviation} = \sqrt{\frac{1}{N}\sum_{1}^{N}(pv_i - \overline{pv})^2}, \quad [12]$$

where N is the number of pixels in the array. Next, the absolute difference between each pixel value and the initial average is computed, and a pixel is discarded from the array if the absolute difference between it and the initial average is greater than twice the RMS Deviation. This may be mathematically represented as:

Discard $pv_i$ if $|pv_i - \overline{pv}| > \gamma \cdot (\text{RMS Deviation})$, $i=1, 2, \ldots N$ [13]

where $\gamma=2$. The corresponding representative value is then generated as an average of the remaining pixel values. In this manner, excessively high and excessively low pixel values are removed, producing a truncated average for the representative value. The excessive values are typically caused by random extraneous radiation, and the above screening and truncation process has the benefit of preventing the excessive values from skewing the representative value. It may be appreciated that the representative value may instead be computed as a truncated median value, a truncated mode value, a truncated percentile value, another type of truncated mean value, and the like, variants thereof, or combinations thereof. It may also be appreciated that other values of $\gamma$ may be used, such as a value in the range of 0.5 to 4, or a value in the range of 1 to 3. The use of equation [13] to reject or disregard non-normal data relates to statistical analysis methods for estimating confidence in data, such as, for example, the Chi-Square Goodness of Fit Test.

First Exemplary Embodiment—Spatial Error Estimation. In a first exemplary embodiment, an estimate for the space-domain error $E_{SPACE}(*)$ is generated at several $X_m$-$Y_n$ grid points for a particular projection r using equation [6], with the number of $X_m$-$Y_n$ grid points typically being much less than the number of pixels in the two-dimensional imager. A common intensity value I1 is used for all of the projections, and the time-domain error $E_{TIME}(*)$ is not estimated. Without loss of generality, the following is used: a two-dimensional imager having x-y dimensions of 40 cm by 30 cm and 1024 pixels by 768 pixels (pixel spacing of 0.388 mm), a spatial modulator 110 having 30 grooves running parallel to the x-dimension, and an $X_m$-$Y_n$ grid having 267 grid points in the $X_m$-dimension and 60 grid points in the $Y_n$-dimension (one per radiation band). (The $X_m$-dimension is parallel to the x-dimension of the imager, and the $Y_n$-dimension is parallel to the y-dimension of the imager.) Some of the $X_m$-$Y_n$ grid points are schematically illustrated in FIG. 5. Representative values $\text{Rep}(X_m, Y_n, r)$ are generated at the $X_m$-$Y_n$ grid points from the spatially modulated measured data $P^M_{MEAS}(x_i, y_j, r)$, as described above. Representative values $\text{Rep}(X_m, Y_n, r)$ at grid points having even-numbered $Y_n$ values (e.g., $Y_2, Y_4, \ldots, n=2, 4, \ldots$) fall within bands where $TP(x,y)=T1$ and, therefore, can be directly used to generate values of the first projection surface $P_{T1}(X_m, Y_n, r)$ at these even-numbered $Y_n$ grid points. Values of the first projection surface $P_{T1}(X_m, Y_n, r)$ at odd-numbered $Y_n$ grid points can be generated by interpolating from the representative values at the even-numbered $Y_n$ grid points. On the other hand, representative values $\text{Rep}(X_m, Y_n, r)$ at $X_m$-$Y_n$ grid points having odd-numbered $Y_n$ values (e.g., $Y_1, Y_3, Y_5, \ldots, n=1, 3, 5, \ldots$) fall within bands where $TP(x,y)=T2$ and, therefore, can be directly used to generate values of the second projection surface $P_{T2}(X_m, Y_n, r)$ at these odd-numbered $Y_n$ grid points. Values of the second projection surface $P_{T2}(X_m, Y_n, r)$ at even-numbered $Y_n$ grid points can be generated by interpolating from the representative values at the odd-numbered $Y_n$ grid points.

More specifically, the representative values $\text{Rep}(X_m, Y_n, r)$ at even-numbered $Y_n$ grid points may be used as estimations of the first projection surface $P_{T1}(X_m, Y_n, r)$ of equation [4] at these grid points as follows:

$$P_{T1}(X_m, Y_n, r) := \text{Rep}(X_m, Y_n, r) \text{ for } m=1, 2, \ldots \text{ and } n=2, 4, 6, \ldots, \quad [14A]$$

where the notation ":=" means that the quantity on the left-hand side is estimated by the quantity on the right-hand side. The values of $P_{T1}(X_m, Y_n, r)$ at odd-numbered $Y_n$ grid points may be generated by interpolating and/or extrapolating (e.g., curve-fitting) from the representative values $\text{Rep}(X_m, Y_n, r)$ at even-numbered $Y_n$ grid points. For example, $P_{T1}(X_m, Y_3, r)$ and $P_{T1}(X_m, Y_5, r)$ may be generated according to the following linear interpolation forms, assuming equal spacing distances between $Y_3$ and each of $Y_2$ and $Y_4$, and between $Y_5$ and each of $Y_4$ and $Y_6$:

$$P_{T1}(X_m, Y_3, r) := 0.5 \cdot \{\text{Rep}(X_m, Y_2, r) + \text{Rep}(X_m, Y_4, r)\},$$
and
$$P_{T1}(X_m, Y_5, r) := 0.5 \cdot \{\text{Rep}(X_m, Y_4, r) + \text{Rep}(X_m, Y_6, r)\}, \text{ for } m=1, 2, \ldots,$$

which may be generalized as:

$$P_{T1}(X_m, Y_n, r) := 0.5 \cdot \{\text{Rep}(X_m, Y_{n-1}, r) + \text{Rep}(X_m, Y_{n+1}, r)\}, \text{ for } m=1, 2, \ldots \text{ and } n=3, 5, \quad [14B]$$

For $P_{T1}(X_m, Y_1, r)$, the following extrapolation form may be used since there is no value of $P_{T1}(X_m, Y_0, r)$ at $Y=Y_0$:

$$P_{T1}(X_m, Y_1, r) := 0.5 \cdot \{3 \cdot \text{Rep}(X_m, Y_2, r) - \text{Rep}(X_m, Y_4, r)\}. \quad [15]$$

In this manner, estimated values for $P_{T1}(X_m, Y_n, r)$ can be obtained for all m and n values for a particular projection from the spatially modulated measured data $P^M_{MEAS}(x_i, y_j, r)$.

Further, the representative values $\text{Rep}(X_m, Y_n, r)$ at grid points having odd-numbered Y values (e.g., $Y_1, Y_3, Y_5, \ldots$, n=1, 3, 5, . . . ) may be used as estimations of the second projection surface $P_{T2}(X_m, Y_n, r)$ of equation [3] as follows:

$$P_{T2}(X_m, Y_n, r) := Rep(X_m, Y_n, r) \text{ for } m=1, 2, \ldots \text{ and } n=1, 3, 5, \quad [16A]$$

The values of $P_{T2}(X_m, Y_n, r)$ at even-numbered $Y_n$ grid points may be generated by interpolating and/or extrapolating (e.g., curve-fitting) from the representative values $Rep(X_m, Y_n, r)$ at odd-numbered $Y_n$ grid points. For example, $P_{T2}(X_m, Y_2, r)$ and $P_{T2}(X_m, Y_4, r)$ may be generated as estimates according to the following linear interpolation forms, assuming equal spacing distances between $Y_2$ and each of $Y_1$ and $Y_3$, and between $Y_4$ and each of $Y_3$ and $Y_5$:

$$P_{T2}(X_m, Y_2, r) := 0.5 \cdot \{Rep(X_m, Y_1, r) + Rep(X_m, Y_3, r)\},$$
and
$$P_{T2}(X_m, Y_4, r) := 0.5 \cdot \{Rep(X_m, Y_3, r) + Rep(X_m, Y_5, r)\}, \text{ for } m=1, 2, \ldots,$$

which may be generalized as:

$$P_{T2}(X_m, Y_n, r) := 0.5 \cdot \{Rep(X_m, Y_{n-1}, r) + Rep(X_m, Y_{n+1}, r)\} \text{ for } m=1, 2, \ldots \text{ and } n=2, 4, 6 \quad [16B]$$

In this manner, estimated values for $P_{T2}(X_m, Y_n, r)$ can be obtained for all m and n values for a particular projection from the spatially modulated measured data $P^M_{MEAS}(x_i, y_j, r)$.

With estimates for $P_{T1}(X_m, Y_n, r)$ and $P_{T2}(X_m, Y_n, r)$, the space-domain error $E_{SPACE}(X_m, Y_n, r)$ at the grid points can be estimated by the application of equation [6] as follows:

$$E_{SPACE}(X_m, Y_n, r) := \{P_{T2}(X_m, Y_n, r) - T \cdot P_{T1}(X_m, Y_n, r)\} / (1 - T), \quad [17]$$

where $T = T2/T1$. For this first exemplary embodiment, the above form can be rewritten in terms of the representative values as given by equations [18] below:

For $Y_n = Y_1$ (extrapolation is used since there is no value of $Rep(X_m, Y_0, r)$ at $Y = Y_0$):

$$E_{SPACE}(X_m, Y_1, r) := Rep(X_m, Y_1, r)/(1-T) - 0.5 \cdot \{3 \cdot Rep(X_m, Y_2, r) - Rep(X_m, Y_4, r)\} \cdot \{T/(1-T)\} \quad [18A]$$

For $Y_n = Y_2, Y_4, Y_6 \ldots$ (even-numbered $Y_n$ grid points):

$$E_{SPACE}(X_m, Y_n, r) := 0.5 \cdot \{Rep(X_m, Y_{n-1}, r) + Rep(X_m, Y_{n+1}, r)\}/(1-T) - T \cdot Rep(X_m, Y_n, r)/(1-T). \quad [18B]$$

For $Y_n = Y_3, Y_5, Y_7 \ldots$ (odd-numbered $Y_n$ grid points):

$$E_{SPACE}(X_m, Y_n, r) := Rep(X_m, Y_n, r)/(1-T) - 0.5 \cdot \{Rep(X_m, Y_{n-1}, r) + Rep(X_m, Y_{n+1}, r)\} \cdot \{T/(1-T)\}. \quad [18C]$$

With $E_{SPACE}(X_m, Y_n, r)$ generated according to equations [18] on the $X_m$-$Y_n$ grid, the space-domain error may be generated for each pixel location $(x_i, y_j)$ by any known interpolation and extrapolation procedures to provide $E_{SPACE}(x_i, y_j, r)$. The generation of the space-domain error from equations [18] does not directly use the projection surfaces $P_{T1}(X_m, Y_n, r)$ and $P_{T2}(X_m, Y_n, r)$. It will be appreciated by those of ordinary skill in the art that the space-domain error can also be generated using equations [14]-[17], where estimated values for the projection surfaces are generated. Such an approach may be used when higher-order interpolation methods are used.

While the first exemplary embodiment and further exemplary embodiments provided below are illustrated using constant values of T1 and T2 for TP(x,y) in the even- and odd-numbered bands, the values TP(x,y) within even-numbered bands may vary slightly from T1 and the values TP(x,y) within odd-numbered bands may vary slightly from T2, such as with a flat-plate modulator like modulator 110. As indicated above, the variation is due to the radiation passing through the flat plate at angles that deviate from perpendicular. The variations from T1 and T2 over the x- and y-domains can be measured in a calibration step (as described above), and recorded for subsequent use. In another exemplary embodiment described below, we show how the variations from T1 and T2 can be determined without a calibration step when using a modulator having regions of a third thickness value (producing transmission factors T3) and additional processing.

Figure 6:
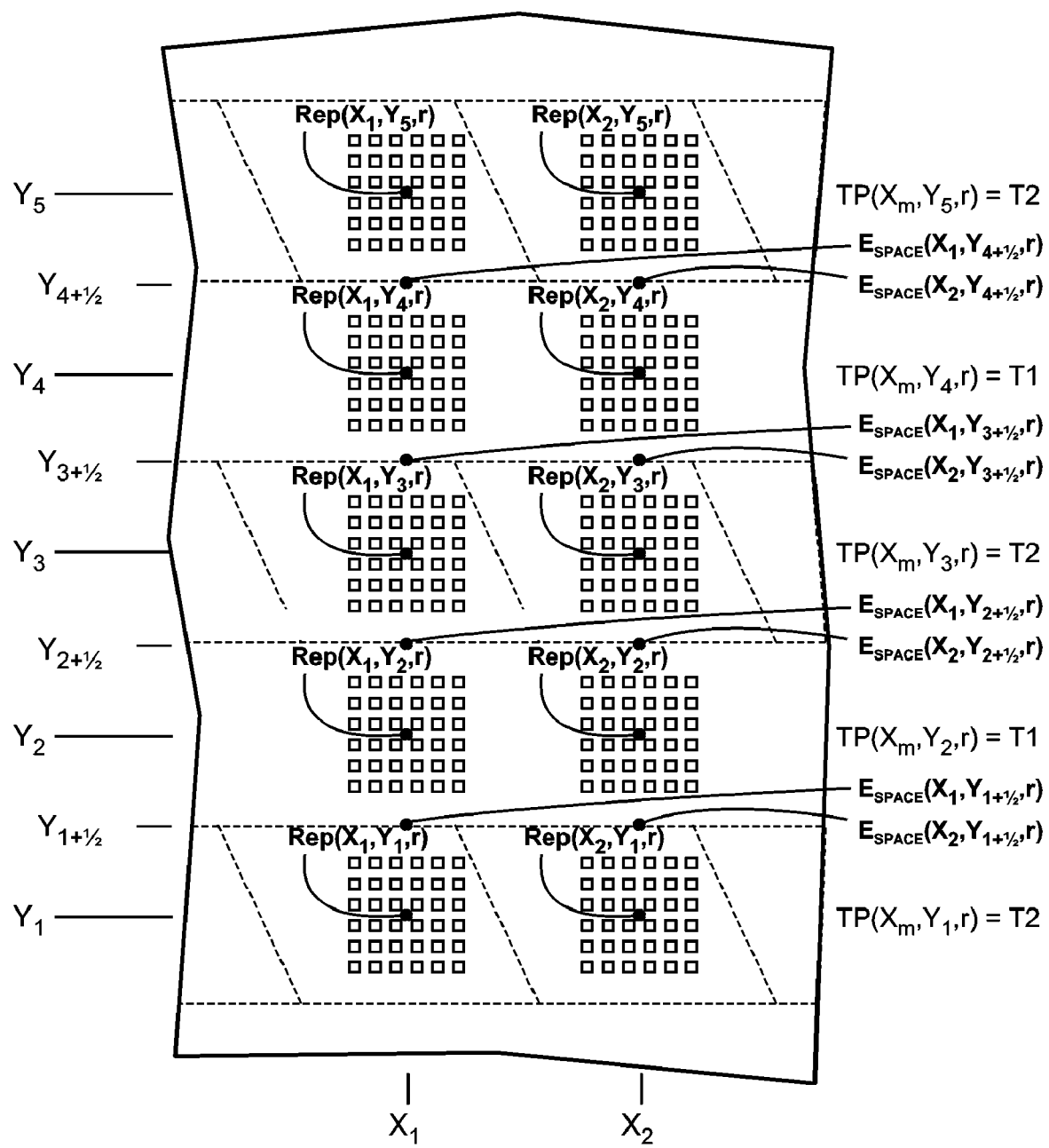
FIG. 6 shows a portion of a two-dimensional imager to illustrate an exemplary embodiment of an invention of the present application.

Second Exemplary Embodiment—Spatial Error Estimation. A second exemplary correction for space-domain errors is described which is simpler than the first exemplary correction embodiment described above. As in the first exemplary embodiment, the representative values $Rep(X_m, Y_n, r)$ are generated on the above-described $X_m, Y_n$ grid. However, as illustrated in FIG. 6, estimated values of the space-domain error $E_{SPACE}(*)$ will not be assigned to points to points on the $X_m$-$Y_n$ grid, but instead will be assigned to points on an intermediate $X'_m, Y'_n$ grid that is shifted by half of a grid spacing in the Y-dimension. In other words, the estimated values of $E_{SPACE}(*)$ are generated for a grid having X values of $X_1, X_2, \ldots$ and Y values of $Y_{1+1/2}, Y_{2+1/2}, Y_{3+1/2}, Y_{4+1/2}, \ldots$, where $Y_{1+1/2} = 0.5 \cdot (Y_1 + Y_2)$, $Y_{2+1/2} = 0.5 \cdot (Y_2 + Y_3)$, $Y_{3+1/2} = 0.5 \cdot (Y_3 + Y_4)$, $Y_{4+1/2} = 0.5 \cdot (Y_4 + Y_5)$, etc. The grid points of the second $X'_m$-$Y'_n$ grid lie near or on the boundary lines between T1 and T2 regions. However, the space-domain error $E_{SPACE}(X_m, Y_{n+1/2}, r)$ is not generated from representative values located on the second $X'_m$-$Y'_n$ grid, but from representative values located on the original $X_m$-$Y_n$ grid. Specifically, the space-domain error $E_{SPACE}(X_m, Y_{n+1/2}, r)$ is estimated using equation [6] with $P_{T2}(X_m, Y_{n+1/2}, r)$ being estimated by the nearest representative value $Rep(X_m, Y_n, r)$ having an odd-numbered $Y_n$ value (e.g., $Y_1, Y_3, Y_5, Y_5, \ldots$), and $P_{T1}(X_m, Y_{n+1/2}, r)$ being estimated by the nearest representative value $Rep(X_m, Y_n, r)$ having an even-numbered $Y_n$ value (e.g., $Y_2, Y_4, \ldots$). This can be mathematically represented as:

For odd values of n, and m=1,2,, . . .

$$E_{SPACE}\left(X_m, Y_{n+\frac{1}{2}}, r\right) := \{P_{T2}(X_m, Y_n, r) - T \cdot P_{T1}(X_m, Y_{n+1}, r)\} / \quad [19A]$$
$$(1 - T)$$
$$:= \{Rep(X_m, Y_n, r) - T \cdot Rep(X_m, Y_{n+1}, r)\} /$$
$$(1 - T).$$

For even values of n, and m=1,2, . . .

$$E_{SPACE}\left(X_m, Y_{n+\frac{1}{2}}, r\right) := \{P_{T2}(X_m, Y_{n+1}, r) - T \cdot P_{T1}(X_m, Y_n, r)\} / \quad [19B]$$
$$(1 - T)$$
$$:= \{Rep(X_m, Y_{n+1}, r) - T \cdot Rep(X_m, Y_n, r)\} /$$
$$(1 - T).$$

With the above generated estimates of the space-domain error $E_{SPACE}(X_m, Y_{n+1/2}, r)$, estimates for the space-domain error may be generated for any and all of the pixels using any conventional interpolation and/or extrapolation method.

The first and second exemplary embodiments may be used in applications where the time-domain error $E_{TIME}(*)$ is low, and not in need of correction. These embodiments may also be used in applications where the space-domain error $E_{SPACE}(*)$ is estimated and removed from the measured data, and where a second process thereafter estimates the time-domain error $E_{TIME}(*)$ and removes that error from the measured data.

Accuracy Considerations for the First and Second Exemplary Embodiments. In the first and second exemplary embodiments, the projection surfaces $P_{T1}(*)$ and $P_{T2}(*)$ are estimated from representative values that are generated using interpolation, extrapolation, and data smoothing of the measured pixel values. These procedures can introduce errors in the estimate of the space-domain error. Analytical and numerical analysis indicates that the amount of error introduced by these procedures generally decreases as the smoothness of space-domain error $E_{SPACE}(x,y,r)$ increases. That is, the estimation of $E_{SPACE}(x,y,r)$ has the best accuracy when $E_{SPACE}(x,y,r)$ is slowly varying over the x- and y-domains of the imager. As indicated above, two primary components of the space domain-error are scattering events and point-spread effects (PSF) in the two-dimensional imager. For typical objects, the scattering events are generated from a large volume of material (which includes both the object and any support platform for the object), and this tends to generate a scattering error that slowly varies over the x- and y-domains of the imager since scattering events are generated by the object over a large extent in these domains. As to the point-spread effects, while each individual point-spread function (PSF) may have a steep tent-like shape (not generally smooth), it is fairly stable with time and the aggregate of the PSFs of all of the pixels is relatively smooth. Accordingly, it is currently believed that $E_{SPACE}(x,y,r)$ is slowly varying over the x- and y-domains for typical objects, and that the data-smoothing, interpolation, and extrapolation procedures introduce only small errors into the estimate for $E_{SPACE}(x,y,r)$. At present, it is believed that the accuracy for the estimate of $E_{SPACE}(x,y,r)$ can be increased by having the width of each radiation band (which corresponds to groove or strip in the plate of spatial modulator 110) be greater than at least twice the full-width of the point-spread function (PSF), as measured at one-tenth of maximum value closest to the center of the PSF. (The PSF can have long tails past the one-tenth maximum locus, with or without ripples.) It is also believed that accuracy can be increased by using a size and shape of the pixel array that keeps the pixel within the width of its corresponding radiation band, preferably centered therein, and preferably within about one-half the width of the radiation band. It is also believed that accuracy can be increased by selecting a size and shape of the pixel array such that the locus of points at the full width of the PSF, as measured at one-tenth of maximum value closest to the center of the PSF, remains within the pixel array. The PSF does not need to be symmetric or the same for each pixel to assure accuracy. The PSF can be empirically measured. If desired, the shapes of the pixel arrays can be varied to follow the contours of the one-tenth maximum loci at the $X_m$–$Y_n$ grid points.

Method, Computer Program Product, and System Implementations of the Spatial-Error Estimation Inventions. We now broadly describe methods and computer program products of the spatial-error correction invention that was just illustrated by the First and Second Exemplary Embodiments. These inventions broadly include methods of generating an estimate of a spatial error in a radiographic projection of an object. The methods broadly comprise obtaining a first radiographic projection of an object, the first projection having a first portion generated from incident radiation having a first magnitude, a second portion generated from incident radiation having a second magnitude that is different from the first magnitude, and ratio T of the second magnitude to the first magnitude. The projection may be obtained by causing the projection to be generated by imaging equipment, or by receiving a projection that has already been generated. The ratio T may be received by the methods as an input quantity, or it may be estimated from the projection data (which is further illustrated below by another exemplary embodiment). The methods further broadly comprise generating an estimate of a spatial error for a first area of the first projection, the first area being located in one of the first and second portions or located between the first and second portions, with the estimate being generated from at least a projection value in the first portion, a projection value in the second portion, and the ratio T. Specific implementations of these actions have been provided above. In addition, the methods further preferably comprise storing the estimate in a computer-readable medium. The methods may include the use of interpolation or extrapolation of the data, as described above, in which case the methods may further generate the estimate from a projection value in a third portion of the projection that is generated from incident radiation having either the first or second magnitude. The methods may also include generating representative values of the projection values in the first and second portions, and generating the estimate of the spatial error from the representative values, as described in detail above. These inventions may also include methods of correcting a radiographic projection of an object for a spatial error, where the methods broadly comprise generating an estimate of the spatial error according to any of the previously described methods, and generating a corrected radiographic projection in relation to a difference of the first radiographic projection and the estimate of the spatial error.

Computer program products for the spatial-error correction inventions generally comprise instruction sets embodied on a tangible computer-readable medium that direct a processor to perform respective actions. As used herein, the term "computer-readable medium" includes volatile memories (e.g., RAM), non-volatile memories (e.g., ROM, EEPROM), disks, magnetic tapes, CD-ROMs, DVDs, and all other types of computer-readable memories. FIG. 11 illustrates the broad embodiments of the computer program products, which shows four instructions sets. Instruction set #1 directs the data processor to obtain the first radiographic projection, as described above. Instruction set #1 may direct the data processor to receive the projection from a computer-readable medium, and/or may direct the data processor to instruct equipment, such as shown in FIG. 2, to obtain the radiographic projection. The second instruction set directs the data processor to generate an estimate of the spatial error, as described above. The second instruction set may include sub-instructions that direct the data processor to generate representative values and perform interpolation and/or extrapolation, as described above. The third instruction set directs the data processor to store the estimate in a writable computer-readable medium. These first three general instruction sets may be used by computer program products for generating estimates of the spatial errors. Computer program products for generating corrected radiographic projections may include these instruction sets as well as optional instruction Set #4, which directs the data processor to generate a corrected radiographic projection in relation to a difference of the first radiographic projection the estimate of the spatial error. The computer program products described herein may be stored in the instruction memory of system 100 shown in FIG. 2 and executed by the data processor of system 100.

Systems according to these inventions may include a processor, a memory, and any of the above computer program products embodied in the memory, and may further include additional components of systems 100 shown in FIG. 2.

Figure 7:
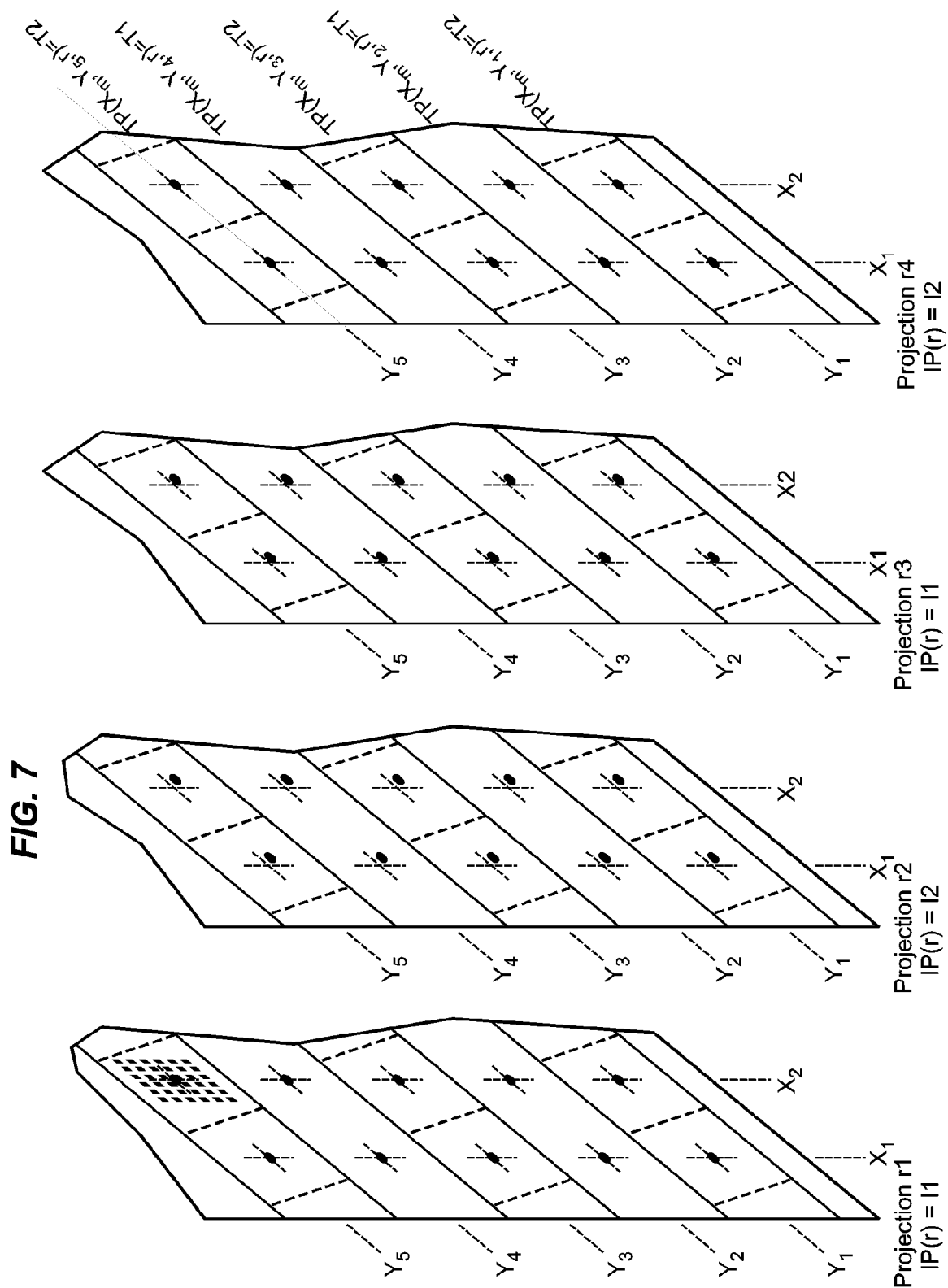
FIG. 7 shows a portion of a two-dimensional imager replicated for four successive projections to illustrate an exemplary embodiment of an invention of the present application.

Third Exemplary Embodiment—Spatial and Temporal Error Estimations. In the third exemplary embodiment, estimates of the space-domain $E_{SPACE}(X_m, Y_n, r)$ are generated at several $X_m$-$Y_n$-r grid points using equations [9C] and [10C] as a framework, and estimates of the time-domain error $E_{TIME}$($X_m$,$Y_n$,r) are generated at several $X_m$-$Y_n$-r grid points using equations [11C] and [11D] as a framework. Once these estimates are generated at their $X_m$-$Y_n$-r grid points, they can be generated for each pixel location ($x_i$,$y_j$) and each projection r by any conventional interpolation or extrapolation method to provide $E_{TIME}$($x_i$,$y_j$,r). FIG. 7 shows a portion of the two-dimensional imager replicated for four successive projections: r1, r2, r3, r4. As in FIGS. 5 and 6, the portion of the two-dimensional imager includes ten grid points (shown as solid dots in the figure) at the $X_m$-coordinate locations of X1 and X2 and the $Y_m$-coordinate locations Y1, Y2, Y3, Y4, and Y5. As before, the portion has three bands where the image is produced with the transmission function TP(X,Y) equal to T2, which are interspersed between four bands where the image is produced with the transmission function TP(X,Y) equal to T1. Associated with each grid point is an array of one or more pixels from which a representative value for the $X_m$-$Y_n$ grid point is generated, as described above. For the sake of visual clarity, only one exemplary array of grid points is shown in the figure.

In the third exemplary embodiment, the radiation source outputs a first intensity I1 for odd-numbered projections ro, and a second intensity I2 for even-numbered projections re, with intensities I1 and I2 being different. The change in projection angles between adjacent projections is assumed to be small so that configurations C1 and C2 are substantially the same. The source's radiation intensity can be readily controlled and changed between levels I1 and I2 by changing the source power (e.g., source current) applied to radiation generator (e.g., X-ray tube). The radiation generator is typically driven by a power amplifier (included as part of the radiation source shown in FIG. 2), which can be configured to receive an analog or digital input signal that designates a desired amount of applied power (e.g., applied source current). As shown in FIG. 2, that input signal is provided by the controller in radiation imaging system 100. In practice, there may be slight deviations from the designated intensities I1 and I2 at particular projections, and procedures to account for these deviations are discussed below.

In this embodiment, the representative values Rep($X_m$, $Y_n$,$r_k$) at grid points on odd-numbered projections ro (e.g., r1, r3, r5, ..., k=1, 3, 5, ...) are used to generate estimations of the projection surfaces $P_{I1,T1}$($X_m$,$Y_n$,ro) and $P_{I1,T2}$($X_m$,$Y_n$,ro) at these grid points. These surfaces may be generated according to equations [14]-[16] where $P_{I1,T1}$($X_m$,$Y_n$,ro) is used in place of $P_{T1}$($X_m$,$Y_n$,ro) and $P_{I1,T2}$($X_m$,$Y_n$,ro) is used in place of $P_{T2}$($X_m$,$Y_n$,ro). The representative values used in this exemplary embodiment are based on the spatially-modulated measured data $P^M_{MEAS}$(x,y,r), as described above. The values of projection surfaces $P_{I1,T1}$($X_m$,$Y_n$,r) and $P_{I1,T2}$($X_m$,$Y_n$,r) at grid points on even-numbered projections re (e.g., r2, r4, r6, ..., k=2, 4, 6, ...) may be generated from interpolation and/or extrapolation (e.g., curve-fitting) of the values of corresponding values of $P_{I1,T1}$($X_m$,$Y_n$,r) and $P_{I1,T2}$($X_m$,$Y_n$,r) at grid points on adjacent odd-numbered projections, such as:

$$P_{I1,T1}(X_m, Y_n, r_k) := 0.5 \cdot \{P_{I1,T1}(X_m, Y_n, r_{k-1}) + P_{I1,T1}(X_m, Y_n, r_{k-1})\}, \text{ and} \quad [20A]$$

$$P_{I1,T2}(X_m, Y_n, r_k) := 0.5 \cdot \{P_{I1,T2}(X_m, Y_n, r_{k-1}) + P_{I1,T2}(X_m, Y_n, r_{k+1})\}, \text{ for, } m=1,2,\ldots, n=1,2,\ldots, \text{ and } k=2, 4, 6, \quad [20B]$$

Equations [20A] and [20B] may be directly expressed in terms of representative values by expanding the right-hand side terms with equations [14]-[16]. In the above way, $P_{I1,T1}$($X_m$,$Y_n$,$r_k$) and $P_{I1,T2}$($X_m$,$Y_n$,$r_k$) can be obtained for all m, n, and k values from the spatially-modulated measured data $P^M_{MEAS}$(x,y,r) (e.g., both odd- and even-numbered projections).

In a corresponding manner, the representative values Rep($X_m$, $Y_n$,$r_k$) at grid points on even-numbered projections re (e.g., r2, r4, r6, ..., k=2, 4, 6, ...) are used to generate estimations of the projection surfaces $P_{I2,T1}$($X_m$,$Y_n$,re) and $P_{I2,T2}$($X_m$,$Y_n$,re) at these grid points. These surfaces may be generated according to equations [14]-[16] where $P_{I2,T1}$($X_m$,$Y_n$,ro) is used in place of $P_{T1}$($X_m$,$Y_n$,ro) and $P_{I2,T2}$($X_m$,$Y_n$,ro) is used in place of $P_{T2}$($X_m$,$Y_n$,ro). The values of projection surfaces $P_{I2,T1}$($X_m$,$Y_n$,r) and $P_{I2,T2}$($X_m$,$Y_n$,r) at grid points on odd-numbered projections ro (e.g., r1, r3, r5, ..., k=1, 3, 5, ...) may be generated from interpolation and/or extrapolation (e.g., curve-fitting) of the values of corresponding values of $P_{I2,T1}$($X_m$,$Y_n$,r) and $P_{I2,T2}$($X_m$,$Y_n$,r) at grid points on adjacent even-numbered projections, such as:

$$P_{I2,T1}(X_m, Y_n, r_k) := 0.5 \cdot \{P_{I2,T1}(X_m, Y_n, r_{k-1}) + P_{I2,T1}(X_m, Y_n, r_{k-1})\}, \text{ and} \quad [21]$$

$$P_{I2,T2}(X_m, Y_n, r_k) := 0.5 \cdot \{P_{I2,T2}(X_m, Y_n, r_{k-1}) + P_{I2,T2}(X_m, Y_n, r_{k+1})\}, \text{ for, } m=1,2,\ldots, n=1,2,\ldots, \text{ and } k=3, 5, \quad [21B]$$

For k=1, the following extrapolation may be used since there are no values of the projection surfaces at Y=$Y_0$:

$$P_{I2,T1}(X_m, Y_n, r1) := 0.5 \cdot \{3 \cdot P_{I2,T1}(X_m, Y_n, r2) - P_{I2,T1}(X_m, Y_n, r4)\}, \text{ and} \quad [22A]$$

$$P_{I2,T2}(X_m, Y_n, r1) := 0.5 \cdot \{3 \cdot P_{I2,T2}(X_m, Y_n, r2) - P_{I2,T2}(X_m, Y_n, r4)\}, \quad [22B]$$

Equations [21] and [22] may be directly expressed in terms of representative values by expanding the right-hand side terms with equations [14]-[16]. In the above way, $P_{I2,T1}$($X_m$,$Y_n$,$r_k$) and $P_{I2,T2}$($X_m$,$Y_n$,$r_k$) can be obtained for all m, n, and k values from the spatially-modulated measured data $P^M_{MEAS}$(x,y,r) (e.g., both odd- and even-numbered projections).

With the above estimates of $P_{I1,T1}$(*), $P_{I1,T2}$(*), $P_{I2,T1}$(*), and $P_{I2,T2}$(*) for the $X_m$-$Y_n$-$r_k$ grid points, $E_{SPACE}$($X_m$,$Y_n$,re) at even-numbered projections may be estimated by application of equation [9C], and $E_{SPACE}$($X_m$,$Y_n$,ro) at odd-numbered projections may be estimated by application of equation [10C]. Also, an estimate of $E_{SPACE}$($X_m$,$Y_n$,re) for an even-numbered projection re can be generated by using the interpolated surfaces generated from representative values from adjacent odd-numbered projections in equation [9C], and this value may be averaged with the estimate $E_{SPACE}$($X_m$, $Y_n$,re) generated from representative values of the even-numbered projection re. In a similar manner, an estimate of $E_{SPACE}$($X_m$,$Y_n$,ro) for an odd-numbered projection re can be generated by using the interpolated surfaces generated from representative values from adjacent even-numbered projections in equation [10C], and this value may be averaged with the estimate $E_{SPACE}$($X_m$, $Y_n$,ro) generated from representative values of the odd-numbered projection ro. $E_{SPACE}$($X_m$, $Y_n$,r) may then be interpolated and/or extrapolated to all pixel locations ($x_i$,$y_j$) to provide $E_{SPACE}$($x_i$,$y_j$,r). It may also be appreciated that the application of equations [9C] and [10C] may be implemented using the representative values, and does not require the actual direct generation of the projection surfaces $P_{I1,T1}$(*), $P_{I1,T2}$(*), $P_{I2,T1}$(*), and $P_{I2,T2}$(*).

Estimates of $E_{TIME}$($X_m$, $Y_n$,r) at locations where TP($X_m$, $Y_n$)=T1 may be generated by using estimates of surfaces $P_{I1,T1}$($X_m$, $Y_n$,r) and $P_{I2,T1}$($X_m$, $Y_n$,r) in equation [11C], and estimates of $E_{TIME}$($X_m$, $Y_n$,r) at locations where TP($X_m$, $Y_n$)=T2 may be generated by using estimates of surfaces $P_{I1,T2}$($X_m$, $Y_n$,r) and $P_{I2,T2}$($X_m$, $Y_n$,r) in equation [11D]. It may also be appreciated that the application of equations [11C] and [11D] may be implemented using the representative values, and does not require the actual direct generation of the projection surfaces $P_{I1,T1}(*)$, $P_{I1,T2}(*)$, $P_{I2,T1}(*)$, and $P_{I2,T2}(*)$. $E_{(Xm,Yn}r)$ may then be interpolated and/or extrapolated to all pixel locations $(x_i,y_j)$ to provide $E_{TIME}(x_i,y_j,r)$. Equation [8] may then be used to generate an estimate the true projection $P_{TRUE}(x_i,y_j,r)$ from $P^M{}_{MEAS}(x_i,y_j,r)$, IP(r), TP($x_i$, $y_j$), $E_{SPACE}(x_i,y_j,r)$, and $E_{TIME}(x_i,y_j,r)$.

The above implementation of the third exemplary embodiment assumes that radiation intensity does not vary from the designated value of I1 for odd-numbered projections and I2 for even-numbered projections. In practice, there may be slight deviations from these values. To improve the accuracy of both the estimation of the time-domain error $E_{TIME}(x,y,r)$ and the actual projection data used for tomographic reconstruction, the intensity of the radiation source can be measured for each projection by the intensity monitor (FIG. 2), and the measured values may be used for I1 and I2. As another option, the measured data $P^M{}_{MEAS}(x_i,y_j,r)$ and representative values can be corrected based on the measured intensity values. For example, if the quantity IM(r) represents the measured intensity for the projections, then the measured data $P^M{}_{MEAS}(x_i,y_j,r)$ at odd-numbered projections r can be corrected by the factor I1/IM(r), and the measured data $P^M{}_{MEAS}(x_i,y_j,r)$ at even-numbered projections r can be corrected by the factor I2/IM(r). Corrections made to $P^M{}_{MEAS}(x_i,y_j,r)$ may be done before the representative values Rep($X_m$, $Y_n$,r) are generated from the measured data. As another approach, the representative values Rep($X_m$, $Y_n$,r) may be generated from uncorrected measured data, and then the correction factor may be applied to the representative values. In the latter case, the correction factors would still have to be applied to the measured data $P^M{}_{MEAS}(x_i,y_j,r)$ in order to improve the accuracy of the projection data. It may be appreciated that the measured data and representative values used in the above-described first and second exemplary embodiments, as well as the further embodiments described below, may be corrected in a similar manner.

Figure 8:
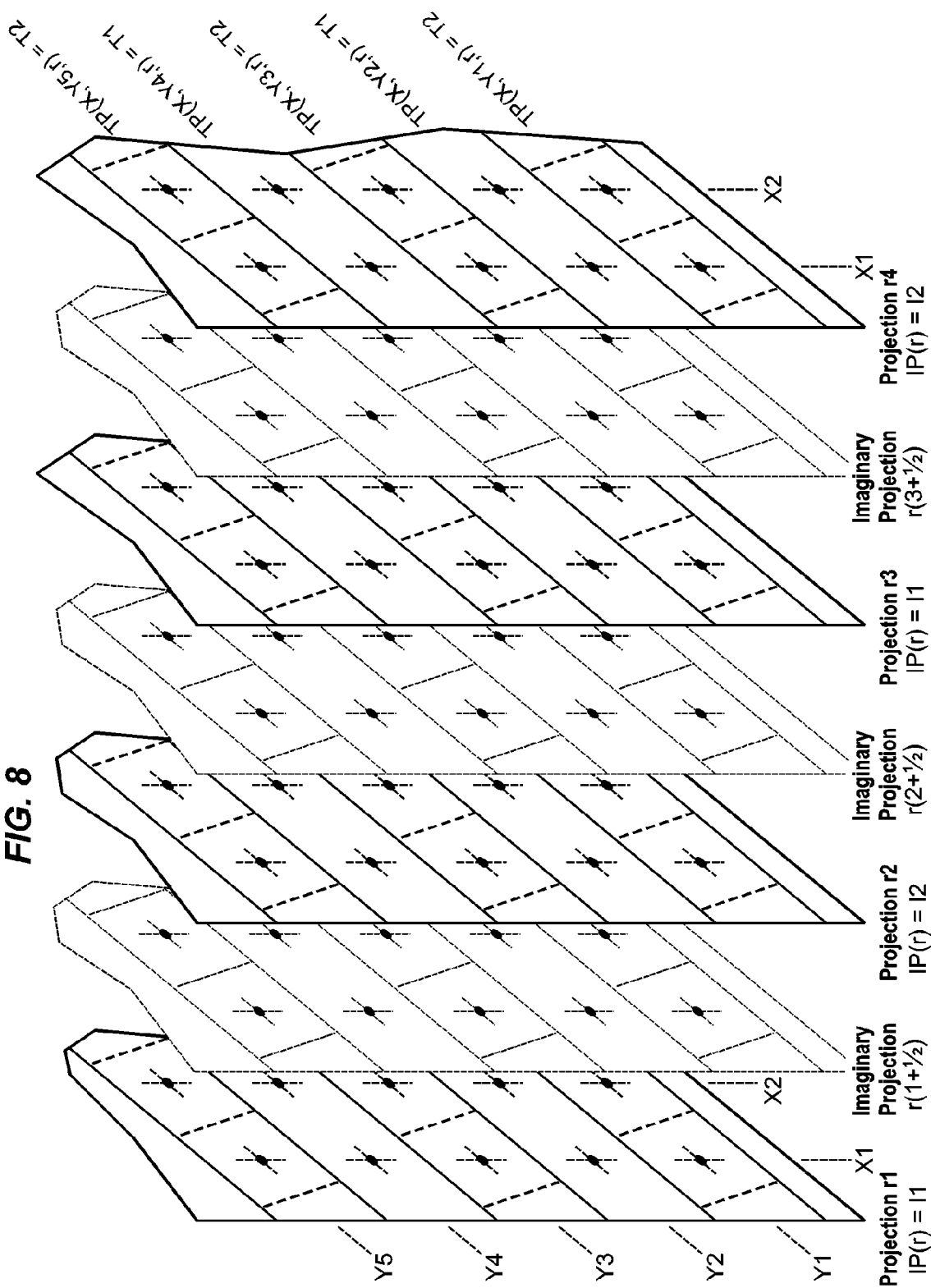
FIG. 8 shows a portion of a two-dimensional imager replicated for four successive projections to illustrate an exemplary embodiment of another invention of the present application.

Fourth Exemplary Embodiment—Spatial and Temporal Error Estimations. In the fourth exemplary embodiment, estimates of the space-domain $E_{SPACE}(X_m,Y_n,r)$ are generated at several $X_m$–$Y_n$–r grid points in the same manner as described for the Third Exemplary Embodiment, and estimates of the time-domain error $E_{TIME}(X_m,Y_n,r)$ are generated at several grid points using equations [11C] and [11D] in a more simple manner than that of the third exemplary embodiment. As in the third exemplary embodiment, the representative values Rep($X_m$, $Y_n$,$r_k$) are generated on the above-described $X_m$–$Y_n$–$r_k$ grid from the spatially-modulated measured data $P^M{}_{MEAS}(x_i,y_j,r)$. However, as illustrated in FIG. 8, estimated values of the time-domain error $E_{TIME}(*)$ are generated on a second $X_m$–$Y_n$–$r_{k+1/2}$ grid that has the same $X_m$–$Y_n$ grid, but are disposed on imaginary projections that are interspersed between the real projections $r_k$ at the halfway points (in time) between the real projections. These imaginary projections are indexed as $r_{k+1/2}$; they are introduced as an interpolation framework, and do not have real intensity values associated with them. Then, the time-domain error $E_{TIME}(X_m,Y_n,r_{k+1/2})$ is estimated for the second grid using equations [11C] and [11D], with $P_{I1,T1}(X_m,Y_n,r_{k+1/2})$ and $P_{I1,T2}(X_m,Y_n,r_{k\ 31\ 1/2})$ being estimated by the nearest representative values on an odd-numbered projection (wherein IP(r)=I1), and with $P_{I2,T1}(X_m,Y_n,r_{k+1/2})$ and $P_{I2,T2}(X_m,Y_n,r_{k+1/2})$ being estimated by the nearest representative values on an even-numbered projection (wherein IP(r)=I2). With these generated estimates of the time-domain error $E_{TIME}(X_m,Y_n,r_{k+1/2})$, m=1, 2, ..., n=1, 2, ..., k=1, 2, ..., estimates for the time-domain error may be generated for any and all of the pixels $(x_i,y_j)$ for the projections r using any conventional interpolation and/or extrapolation method to provide $E_{TIME}(x_i,y_j,r)$. The space-domain error $E_{SPACE}(x_i,y_j,r)$ may be generated in the same manner as was done in the above third exemplary embodiment. Equation [8] may then be used to generate an estimate the true projection $P_{TRUE}(x_i,y_j,r)$ from $P^M{}_{MEAS}(x_i,y_j,r)$, IP(r), TP($x_i,y_j$), $E_{SPACE}(x_i,y_j,r)$, and $E_{TIME}(x_i,y_j,r)$.

Fifth Exemplary Embodiment—Spatial and Temporal Error Estimations. In this approach, the four equations [9A], [9B], [10A], and [10B] are solved for the three unknowns $P_{TRUE}(X_m,Y_n,r)$, $E_{SPACE}(X_m,Y_n,r)$, and $E_{TIME}(X_m,Y_n,r)$ at each of the $X_m$–$Y_n$–r grid points shown in FIG. 7, or each of the $X_m$–$Y_n$–$r_{k+1/2}$ grid points shown in FIG. 8, or at selected ones of the grid points. More specifically, for a selected grid point, estimates of the projection surfaces $P_{I1,T1}(*)$, $P_{I1,T2}(*)$, $P_{I2,T1}(*)$, and $P_{I2,T2}(*)$ are generated as done in any of the above-described exemplary embodiments, and these estimates and equations [9A], [9B], [10A], and [10B] are received by any conventional least squares method, which generates an optimum minimum root-mean-square (RMS) solution for the values of the three unknowns. The estimate of $P_{TRUE}(X_m, Y_n,r)$ generated by the least squares method is generally discarded. The estimates generated for $E_{SPACE}(X_m, Y_n,r)$ and $E_{TIME}(X_m,Y_n,r)$ may be interpolated over the entire pixel array $(x_i,y_j)$ to provide $E_{SPACE}(x_i,y_j,r)$ and $E_{TIME}(x_i,y_j,r)$. The interpolated values may be used in equation [8] to generate values for $P_{TRUE}(x_i,y_j,r)$ over the x- and y-domains of the projection (in the case of the grid of FIG. 7), or over the x- and y-domains of the adjacent projections ro and re (in the case of the grid of FIG. 8). The projection surfaces $P_{I1,T1}(*)$, $P_{I1,T2}(*)$, $P_{I2,T1}(*)$, and $P_{I2,T2}(*)$ are provided in terms of representative values, as described above, and the forms of equations [9A], [9B], [10A], and [10B] provided to the least squares method may be expressed in terms of representative values. This exemplary method can be further extended to include additional surfaces generated from additional transmission values, such as TP=T3, and additional irradiation values, such as IP=I3.

Sixth Exemplary Embodiment—Temporal Error Estimations. In this exemplary embodiment, a spatial modulation has not been used to collect the projection data and only $P_{MEAS}(x,y,r)$ is available, or the modulated projection data $P^M{}_{MEAS}(x,y,r)$ has been corrected for the spatial error, such as through the above-described first and second exemplary embodiments, and $P_{MEAS}(x,y,r)$ has been generated from $P^M{}_{MEAS}(x,y,r)$ using equation [1B]. Thus, this embodiment assumes that the corresponding analog to equation [8] is:

$$P_{MEAS}(x,y,r)=IP(r)\cdot P_{TRUE}(x,y,r)+E_{TIME}(x,y,r) \quad [23]$$

Without loss of generality, the example of intensity-pattern function IP(r) alternating between two intensity values I1 and I2 is examined, with IP(r)=I1 for odd values of projections r, and IP(r)=I2 for even values of projections r. As before, the odd projections will be denoted as ro, and the even projections will be denoted as re. This is a two-tier time-domain modulation that is similar to the two-tier modulation (T1,T2) produced by the space modulator.

By sampling the measurement $P_{MEAS}(x,y,ro)$ on an $X_m$–$Y_n$ grid of points for odd-numbered projections (IP(ro)=I1), a projection surface $P_{I1}(X_m,Y_n,ro)$ based on equation [23] can be obtained for the odd projections ro:

$$P_{I1}(X_m,Y_n,ro,C1)=I1\cdot P_{TRUE}(X_m,Y_n,ro,C1)+E_{TIME}(X_m,Y_n,ro,C1) \quad [24]$$

where the parameter C1 represents the system configuration for the particular value of ro, e.g., the projection angle of the projection. A similar projection surface can be obtained for the second intensity level I2 during the even-numbered projections. Specifically, by sampling the measurement $P_{MEAS}$(x,y,re) on an $X_m$-$Y_n$ grid of points for even-numbered projections (IP(re)=I2), the following projection surface $P_{I2,T1}$($X_m$,$Y_n$,re,C2) based on equation [23] can be obtained for the even projections re:

$$P_{I2}(X_m, Y_n, re, C2) = I2 \cdot P_{TRUE}(X_m, Y_n, re, C2) + E_{TIME}(X_m, Y_n, re, C2) \quad [25]$$

where the parameter C2 represents the system configuration for the particular value of re, e.g., the projection angle of the projection. Because $E_{TIME}(*)$ is slowly varying with respect to the parameters $X_m$, $Y_n$, r, and C, $E_{TIME}(X_m, Y_n, ro, C1)$ and $E_{TIME}(X_m, Y_n, re, C2)$ should be very close in value for adjacent projections re and ro where C1 and C2 are only slightly different. Also, since the projections $P_{I1}(*)$ and $P_{I2}(*)$ are generated from coarse $X_m$-$Y_n$ grids, the variables $P_{TRUE}(*)$ in equations [24] and [25] will effectively be slowly varying. Thus, equations [24] and [25] may be viewed as two equations in two unknowns, $P_{TRUE}(X_m, Y_n, r)$ and $E_{TIME}(X_m, Y_n, r)$, which can be solved. The solution is provided by:

$$E_{TIME}(X_m, Y_n, r) := \{P_{I1}(X_m, Y_n, r) - (I1/I2) \cdot P_{I2}(X_m, Y_n, r)\}/\beta \quad [26]$$

where $\beta = (1 - I1/I2)$.

Accordingly, estimates for $P_{I1}(X_m, Y_n, r)$ and $P_{I2}(X_m, Y_n, r)$ may generated for the $X_m$-$Y_n$-r grid shown in FIG. 7 from representative values using equations [20A], [21A], and [22A] with $P_{I1}(X_m, Y_n, r)$ used in place of $P_{I1,T1}(X_m, Y_n, r)$, and $P_{I2}(X_m, Y_n, r)$ used in place of $P_{I2,T1}(X_m, Y_n, r)$. Equation [26] may then be applied to these estimates to generate $E_{TIME}(X_m, Y_n, r)$ for the grid points. The estimates of $E_{TIME}(X_m, Y_n, r)$ may be interpolated over the entire pixel array ($x_i$,$y_j$) to provide $E_{TIME}(x_i, y_j, r)$, and $P_{TRUE}(x_i, y_j, r)$ may be generated for the entire pixel array by using equation [23], or more specifically:

$$P_{TRUE}(x_i, y_j, r) = \{P_{MEAS}(x_i, y_j, r) - E_{TIME}(x_i, y_j, r)\}/IP(r). \quad [27]$$

As another approach, estimates for $P_{I1}(X_m, Y_n, r_{k+1/2})$ and $P_{I2}(X_m, Y_n, r_{k+1/2})$ may be generated for the $X_m$-$Y_n$-$r_{k+1/2}$ grid shown in FIG. 8 by using the nearest representative values. Equation [26] may then be applied to these estimates to generate $E_{TIME}(X_m, Y_n, r_{k+1/2})$ for the $X_m$-$Y_n$-$r_{k+1/2}$ grid points The estimates of $E_{TIME}(X_m, Y_n, r_{k+1/2})$ may then be interpolated back to the real projection surfaces and the entire pixel array ($x_i$,$y_j$) using conventional interpolation methods to provide $E_{TIME}(x_i, y_j, r_k)$. $P_{TRUE}(x_i, y_j, r_k)$ may then be generated from equation [27].

Method, Computer-Program Product, and System Implementations of the Spatial- and Temporal-Error Correction Inventions. Methods, computer-program products, and systems of the spatial- and temporal-error correction inventions illustrated by the Third through Fifth Exemplary Embodiments are now described. These inventions broadly include methods of generating estimates of spatial errors and temporal errors in a radiographic projection of an object. The methods broadly comprise obtaining a first radiographic projection of an object and a second radiographic projection of the object, where the first projection has first and second portions generated from radiation of a first magnitude I1 that is passed through a spatial modulator, and where the second projection has first and second portions generated from radiation of a second magnitude I2 that is passed through the spatial modulator, with the second magnitude I2 being different from the first magnitude I1. The spatial modulator is disposed between the radiation source and the object, and creates further differences in the radiation that is incident upon the object and received by the first and second portions of each projection.

The ratio of these differences may be represented by the ratio T that was described for the First and Second Exemplary embodiments, which may be based on the transmission pattern function TP(*). The first portions of the projections typically have the same x-y coordinates on the imager, and the second portions of the projections typically have the same x-y coordinates on the imager. The first and second projections may be obtained by causing the projection to be generated by imaging equipment, or by a receiving projection that has already been generated.

The methods further broadly comprise generating an estimate of a spatial error for a first area of the first projection, the first area being located in one of the first and second portions or located between the first and second portions, with the estimate being generated from at least a projection value in the first portion, a projection value in the second portion, and the ratio T. Specific implementations of these actions have been provided above. The methods further broadly comprise generating an estimate of a temporal error for a second area located in the first or second radiographic projections, or in an imaginary radiographic projection that is disposed in time between the first and second radiographic projections, the temporal error being generated from at least a projection value in the first or second portion of the first radiographic projection, a projection value in the first or second portion of the second radiographic projection, the first magnitude I1, and the second magnitude I2. The second area may be the same as the first area. Specific implementations of these actions have been provided above.

In addition, the methods further preferably comprise storing the estimate in a computer-readable medium. The methods may include the use of interpolation or extrapolation of the data, as described above, in which case the methods may further generate the estimate from a projection value in a first or second portion of a third projection that is generated from incident radiation having either the first magnitude I1 or second magnitude I2. The methods may also include generating representative values of the projection values in the first, second, and third projections, and generating the estimate of the temporal error from the representative values, as described in detail above. This invention also includes methods of correcting a radiographic projection of an object for the spatial and temporal errors, where the methods broadly comprise generating estimates of spatial and temporal errors according to any of the previously described methods, and generating a corrected radiographic projection in relation to one of the radiographic projections and the estimates of the spatial and temporal errors.

Computer program products for implementing the above methods generally comprise instruction sets embodied on a tangible computer-readable medium that direct a processor to perform respective tasks of the methods. FIG. 12, which shows five instruction sets, illustrates the broad embodiments of the computer-program products. Instruction set #1 directs the data processor to obtain the first and second radiographic projections, as described above. Instruction set #1 may direct the data processor to receive the projections from a computer-readable medium, and/or may direct the data processor to instruct equipment, such as that shown in FIG. 2, to obtain the radiographic projections. Instruction set #2 directs the data processor to generate an estimate of the spatial error, as described above. The second instruction set may include sub-instructions that direct the data processor to generate representative values and perform interpolation and/or extrapolation, as described above. Instruction set #3 directs the data processor to generate an estimate of the temporal error, as described above. The third instruction set may include sub-instructions that direct the data processor to generate representative values and perform interpolation and/or extrapolation, as described above. In the case of the Fifth Exemplary Embodiment, the second and third instruction sets may be combined to generate these error estimates with a least-squares method.

Instruction set #4 directs the data processor to store the error estimates in a tangible computer-readable medium. The first four general instruction sets may be used by computer-program products for generating estimates of the spatial and temporal errors. Computer-program products for generating corrected radiographic projections may include these instruction sets as well as instruction Set #5, which directs the data processor to generate a corrected radiographic projection in relation to the first radiographic projection and the error estimates. The computer-program products described herein may be stored in the instruction memory of system 100 shown in FIG. 2 and executed by the data processor of system 100.

Methods, computer-program products, and systems for the above-described Sixth Exemplary embodiment may follow those for the Third through Fifth Exemplary Embodiments, except that estimates of the spatial error are not generated, and instruction Set #2 in FIG. 12 is not used.

Seventh Exemplary Embodiment—Refined Estimate Accounting for Variations in Detector Gain. As previously indicated, an array of semiconductor diodes (i.e., detectors) is used to detect the received radiation and generate an electrical signal in relation to the received radiation. Each diode has carrier traps that capture and hold free electrons and free holes in the semiconductor material for varying periods of time before releasing them. This trapping of carriers causes changes in both the signal-detection gain and signal offset of the diode. The above-described time-domain error $E_{TIME}(x,y,r)$ accounts for both of these changes, as well as other time-domain effects. The inventors have discovered an additional way of accounting for the variations in signal-detection gain to provide estimates of the time domain errors. Specifically, for each diode detector or group of diode detectors in the array, the relative gain $Gr(x,y,r)$ of a detector or a group of detectors at a projection r relative to an initial value is estimated and tracked, and the intensity level of the source radiation is cycled through at least three different levels to assist in the estimation. The relative gain $Gr(x,y,r)$ represents the change in gain relative to an initial condition due to the change in efficiency of free charge sensitivity at the time of measurement. $Gr(x,y,r)$ may be related to its previous values by equation [28]:

$$Gr(x, y, r) = [Gr(x, y, r-1) \cdot Z(x, y, r)] \quad [28]$$

$$= Gr(x, y, -1) \cdot \prod_{n=0}^{n=r} Z(x, y, n)$$

where $Z(x,y,r)$ represents the relative change in the gain of a detector or a group of detectors at a projection r relative to its value at the previous projection. $Gr(x,y,-1)$ is an initial value, which can be selected or estimated, as described below. Because $Gr(x,y,r)$ is slowly varying, $Z(x,y,r)$ has a value near unity. $Z(x,y,r)$ can be viewed as the amount of output signal generated per radiation photon received at projection r divided by the output signal generated per radiation photon received at the previous projection r−1, and it represents the relative change in gain due to the change in efficiency of free charge sensitivity between successive projections. In addition to variations in gain, a detector will usually have variations in its offset value, which we denote as $Og(x,y,r)$ for a diode or a group of diodes. $Og(x,y,r)$ is a time-domain error, and may be merged in with the time-domain error $E_{TIME}(x,y,r)$ as $E'_{TIME}(x,y,r)$.

We begin illustrating the improved methods by developing a framework that can be used on individual diode detectors. We can then draw on this framework to develop methods that are applied on groups of diode detectors. As we have indicated above, there can be occasional random radiation effects in the CT environment that skew individual diodes and their outputs, and the impact of these random effects on computing estimates for $E_{SPACE}(x,y,r)$ and $E_{TIME}(x,y,r)$ can be mitigated by averaging and qualifying the measured data produced by several adjacent detectors (i.e., by using the representative values described above). We begin the framework development by augmenting equation [8] to account for the changes in detector gain as follows:

$$P_{MEAS}^M(x, y, r) = IP(r) \cdot TP(x, y) \cdot [Gr(x, y, r-1) \cdot Z(x, y, r)] \cdot \quad [8']$$

$$P_{TRUE}(x, y, r) +$$

$$Og(x, y, r) + IP(r) \cdot E_{SPACE}(x, y, r) +$$

$$TP(x, y) \cdot E_{TIME}(x, y, r)$$

$$= IP(r) \cdot TP(x, y) \cdot [Gr(x, y, r-1) \cdot Z(x, y, r)] \cdot$$

$$P_{TRUE}(x, y, r) +$$

$$IP(r) \cdot E_{SPACE}(x, y, r) + TP(x, y) \cdot$$

$$E'_{TIME}(x, y, r).$$

$Gr(x,y,r-1)$ is the relative gain at the previous projection, and can be found by equation [28]. The unknowns are $Z(x,y,r)$, $P_{TRUE}(x,y,r)$, $E_{SPACE}(x,y,r)$, and $E'_{TIME}(x,y,r)$. $Gr(x,y,r-1)$ and $Og(x,y,r)$ can be representative of a single detector, or can be representative of a group of detectors clustered around an $X_m$-$Y_n$ grid point since detectors that are close to one another have similar properties.

Relative gain change $Z(x,y,r)$ increases the number of unknowns by one. It can be estimated by adding one or more additional data sets in time. Additional data sets can be generated by using additional values of intensity pattern IP(r), e.g., using three different values instead of two. In one implementation, the projections are arranged in successive groups of three, with the intensity pattern IP(r) being different for each projection of the group. The system configurations of the three successive projections are assumed to be close, so that their system configuration parameters (C1, C2, C3) are assumed to be the substantially same (and are omitted from the notation in this section). Each group of projections is indexed by index R, with the index M=0,1,2 being used to identify the individual projections within each group R. Indices R and M may be related to the base projection index r as follows: (3R+M)=r. Table I gives a sample correspondence of these values:

TABLE I

| | R | | | | | | | | |
|---|---|---|---|---|---|---|---|---|---|
| | 0 | | | 1 | | | 2 | | |
| M | 0 | 1 | 2 | 0 | 1 | 2 | 0 | 1 | 2 |
| 'r' | 0 | 1 | 2 | 3 | 4 | 5 | 6 | 7 | 8 |

The relative projection intensities can be set as follows: $IP(R) = 1-\Delta$, $IP(R+1) = 1$, and $IP(R+2) = 1+\Delta$, which can be expressed as $IP(R+M) = 1+(M-1)\cdot\Delta$, where $\Delta$ is small, such as around 0.1. Because $Z(x,y,r)$ and $E'_{TIME}(x,y,r)$ are slowly varying, each may be assumed to be constant during the three projections of a group: $Z(x,y,3R+M) \approx Z(x,y,3R)$ and $E'_{TIME}(x,y,3R+M) \approx E'_{TIME}(x,y,3R)$.

For each group R, we can write the following three equations based on equation [8']:

$$P^M_{MEAS}(x,y,3R+M) = IP(M)\cdot TP(x,y)\cdot[Gr(x,y,3R-1)\cdot Z(x,y,3R)^{M+1}]\cdot P_{TRUE}(x,y,3R+M) + IP(M)\cdot E_{SPACE}(x,y,3R+M) + TP(x,y)\cdot E'_{TIME}(x,y,3R) \text{ for } M=0, 1, \text{ and } 2. \quad [29]$$

where $P^M_{MEAS}(x,y,3R+M)$, $IP(M)$ and $TP(x,y)$ are known, and where $Gr(x,y,3R-1)$ is known through equation [28] since it is the relative gain at the last projection in the prior group (R−1) of projections. $Z(*)$ and $E'_{TIME}(*)$ can be estimated on a coarse $X_m$-$Y_n$ grid by using equation [29] with the values of $P^M_{MEAS}(x,y,3R+M)$ replaced by representative values $Rep(X_m,Y_n,3R+M)$, which are known, with the values of $P_{TRUE}(X_m,Y_n,3R+M)$ approximated by a single value $P'_{TRUE}(X_m,Y_n,3R)$, which will be taken as an unknown, and with the values of $Gr(X_m,Y_n,3R-1)$ being tracked on the coarse grid. These steps lead to the three equations [30]:

$$Rep(X_m,Y_n,3R+M) = IP(M)\cdot TP(X_m,Y_n)\cdot[Gr(X_m,Y_n,3R-1)\cdot Z(X_m,Y_n,3R)^{M+1}]\cdot P'_{TRUE}(X_m,Y_n,3R) + IP(M)\cdot E_{SPACE}(X_m,Y_n,3R+M) + TP(X_m,Y_n)\cdot E'_{TIME}(X_m,Y_n,3R) \text{ for } M=0, 1, \text{ and } 2 \quad [30]$$

The above three equations can be solved for the unknowns. To simplify the solution, an estimate of the spatial error $E_{SPACE}(X_m,Y_n,r)$ for equations [30] can be found first, such as by using the above-described spatial-solution methods, which leaves $Z(X_m,Y_n,3R)$ and $E'_{TIME}(X_m,Y_n,3R)$ as the unknowns. Because there are multiplication products between the unknowns $Z(X_m,Y_n,3R)$ and $P'_{TRUE}(X_m,Y_n,3R)$ in equations [30], the equations are non-linear. They can be solved using Newton methods, non-linear least squares methods, or linearization approximation techniques. An example of the latter technique is provided below.

Once $Z(X_m,Y_n,3R)$, $Gr(X_m,Y_n,3R-1)$, $E'_{TIME}(X_m,Y_n,3R)$, and $E_{SPACE}(X_m,Y_n,r)$ are estimated on the coarse grid, they may be interpolated over the pixels to provide $Z(x_i,y_j,3R)$, $Gr(x_i,y_j,3R-1)$, $E'_{TIME}(x_i,y_j,3R)$, and $E_{SPACE}(x_i,y_j,r)$. Then, estimates for the true projection $P_{TRUE}(x_i,y_j,3R+M)$ may be generated based on equation [29] as follows:

$$P_{TRUE}(x_i,y_j,3R+M) = \frac{[P^M_{MEAS}(x_i,y_j,3R+M) - IP(M)\cdot E_{SPACE}(x_i,y_j,3R+M) - TP(x_i,y_j)\cdot E'_{TIME}(x_i,y_j,3R)]}{TP(x_i,y_j)\cdot IP(M)\cdot Gr(x_i,y_j,3R-1)\cdot Z(x_i,y_j,3R)^{M+1}} \quad [31]$$

for $M = 0, 1,$ and $2$,

Below, a linearized version of equation [30] is developed, which can be used to find good estimates of the unknowns with a minimum of computation requirements. To simplify the presentation, we will use adjusted representative values $Rep'(X_m,Y_n,3R+M)$ that have been adjusted for the effects of $E'_{SPACE}(X_m,Y_n,3R)$ and $TP(X_m,Y_n)$: $Rep'(X_m,Y_n,3R+M) = \{Rep(X_m,Y_n,3R+M) - IP(M)\cdot E'_{TIME}(x,y,3R)\}/TP(X_m,Y_n)$. Noting that $Z(X_m,Y_n,3R)$ is near unity and can be rewritten as $Z(X_m,Y_n,3R) = 1+\xi(X_m,Y_n,3R)$, where $\xi(X_m,Y_n,3R)$ is small, and further noting that the quantity $[1+\xi(X_m,Y_n,3R)]^{M+1}$ can be approximated as $1+(M+1)\xi(x,y,3R)$, an approximate formulation of equation [30] can be made as follows:

$$Rep'(X_m,Y_n,3R+M) = IP(M)\cdot[Gr(X_m,Y_n,3R-1)\cdot[1+(M+1)\xi(X_m,Y_n,3R)]]\cdot P'_{TRUE}(X_m,Y_n,3R) + E'_{TIME}(X_m,Y_n,3R), \text{ for } M=0, 1, \text{ and } 2 \quad [32]$$

where $\xi(X_m,Y_n,3R)$ replaces $Z(X_m,Y_n,3R)$ as one of the unknowns. Equation [32] has a non-linear term of $\xi(X_m,Y_n,3R)\cdot P'_{TRUE}(X_m,Y_n,3R)$, which can be approximated as $\xi(X_m,Y_n,3R)\cdot Rep(X_m,Y_n,3R+M)$ since $\xi(X_m,Y_n,3R)$ is small. This further approximate formulation may be written in matrix form as follows:

$$\begin{bmatrix} Rep'(X_m,Y_n,3R+0) \\ Rep'(X_m,Y_n,3R+1) \\ Rep'(X_m,Y_n,3R+2) \end{bmatrix} = Mat \cdot \begin{bmatrix} P'_{TRUE}(X_m,Y_n,3R) \\ \zeta(X_m,Y_n,3R) \\ E'_{TIME}(X_m,Y_n,3R) \end{bmatrix} \quad [33]$$

where matrix $$Mat = \begin{bmatrix} \{IP(0)\cdot Gr(X_m,Y_n,3R-1)\} & \{1\cdot IP(0)\cdot Gr(X_m,Y_n,3R-1)\}\cdot Rep'(X_m,Y_n,3R+0) & 1 \\ \{IP(1)\cdot Gr(X_m,Y_n,3R-1)\} & \{2\cdot IP(1)\cdot Gr(X_m,Y_n,3R-1)\}\cdot Rep'(X_m,Y_n,3R+1) & 1 \\ \{IP(2)\cdot Gr(X_m,Y_n,3R-1)\} & \{3\cdot IP(2)\cdot Gr(X_m,Y_n,3R-1)\}\cdot Rep'(X_m,Y_n,3R+2) & 1 \end{bmatrix}.$$

Equation [33] may then be solved by conventional linear solution techniques, including but not limited to LU decomposition and direct forms using determinants of the matrix and sub-matrices. As an option, equation [33] may be solved again with the values of $Rep(X_m,Y_n,3R+M)$ in the second column of matrix Mat replaced with the value for $P'_{TRUE}(X_m,Y_n,3R)$ obtained by the first solution of equation [33]. This can mitigate the errors in initially approximating the non-linear term $\xi(X_m,Y_n,3R)\cdot P'_{TRUE}(X_m,Y_n,3R)$ with $\xi(X_m,Y_n,3R)\cdot Rep(X_m,Y_n,3R+M)$.

After solving equation [33], $Z(X_m,Y_n,3R)$, $Gr(X_m,Y_n,3R-1)$, $E'_{TIME}(X_m,Y_n,3R)$, and $E_{SPACE}(X_m,Y_n,r)$ are interpolated over the pixels to provide $Z(x_i,y_j,3R)$, $Gr(x_i,y_j,3R-1)$, $E'_{TIME}(x_i,y_j,3R)$, and $E_{SPACE}(x_i,y_j,r)$, and $P_{TRUE}(x_i,y_j,3R+M)$ may be estimated from equation [31]. In preparation for the next group of three projections, $Gr(X_m,Y_n,3R+2)$ can be generated as:

$$Gr(X_m, Y_n, 3R+2) = Gr(X_m, Y_n, 3R-1) \cdot$$

$$[1 + 3*\zeta(X_m, Y_n, 3R)]$$

$$\approx Gr(X_m, Y_n, 3R-1) \cdot$$

$$[1 + \zeta(X_m, Y_n, 3R)]^3. \quad [34a]$$

If a non-linear solution method (e.g., Newton's method) has been used to estimate $Z(X_m, Y_n, 3R)$, then $Gr(X_m, Y_n, 3R+2)$ may be generated as:

$$Gr(X_m, Y_n, 3R+2) = Gr(X_m, Y_n, 3R-1)*Z(X_m, Y_n, 3R)^3. \quad [34b]$$

Subsequent projection groups R are processed in a similar manner. For the initial group of projections R=0, a value of or near 1 may be used for $Gr(X_m, Y_n, -1)$. This may cause some error with some detectors and some scan configurations since the source radiation is turned on just prior to the start of the first projection and the detectors are undergoing large changes in their characteristics since they are starting from states with low levels of free and trapped carriers. If a "norm" scan on a calibration phantom object is obtained for the target scan (a target scan being, for example, a scan of a patient), then the errors that affect the starting conditions apply substantially equally to both scans, and the errors can substantially cancel one another when the target scan is normalized to the norm scan. As another approach for minimizing the starting errors, the radiation source can be activated a few seconds before the scan begins to allow the detectors to generate carriers and undergo a substantial portion of their initial changes before the projections are started.

In some instances of solving equation [33], there may be a large difference in magnitudes between the values of $\xi(X_m, Y_n, 3R)$ on the one hand, and values of $P'_{TRUE}(X_m, Y_n, 3R)$ and $E'_{TIME}(X_m, Y_n, 3R)$ on the other hand, which may result in reduced accuracy in the LU decomposition. In these cases, the matrix unknowns and matrix entries may be pre-scaled according to methods known in the matrix solution art. For example, the middle column elements of matrix Mat may be scaled by a constant $\alpha$ so that these matrix elements are close to 1 in value, which would result in the LU decomposition process solving for $\xi(X_m, Y_n, 3R)/\alpha$ instead of $\xi(X_m, Y_n, 3R)$. Thus, equation [33] has a number of mathematically equivalent forms, which differ in their scaling of the matrix elements, knowns, and unknowns, and all of these equivalent forms are encompassed by the present inventions and their corresponding claims.

While the above equations are preferably applied to successive groups of three projections which do not overlap, it may be appreciated that the equations may be applied to projection groups that do overlap. For example, after the first three projections have been processed (R=0, covering r=0, 1, and 2), the equations may be applied, with appropriate modifications, to an overlapping projection group having r=1, 2, and 3. This first overlapping iteration should provide more accurate estimates of the errors and relative gains for the r=2 projection, leading to a better estimate of $P_{TRUE}(x,y,2)$. Then, the next overlapping set of projections can be for r=2, 3, and 4, and the processing thereof providing estimates for the r=3 projection.

Figure 9:
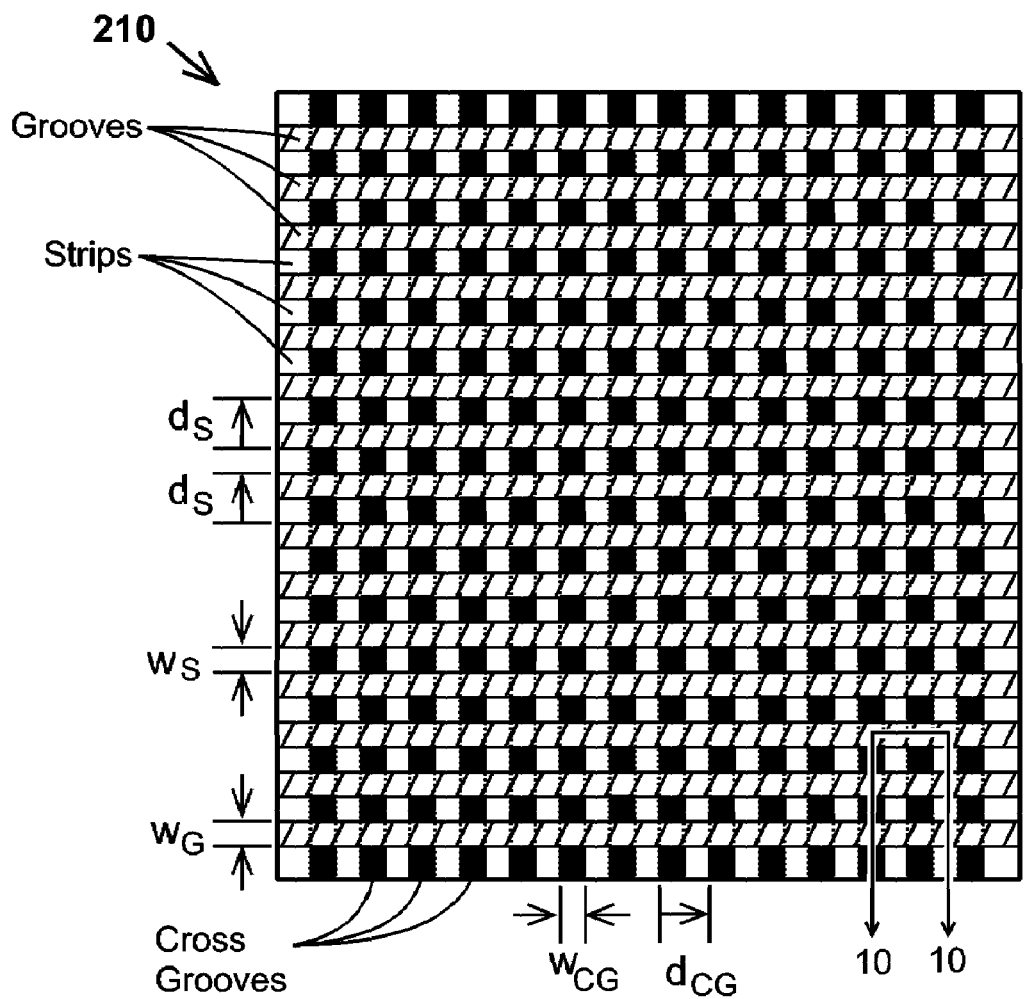
FIG. 9 is a top plan view of a second exemplary spatial modulator according to inventions of the present application.
Figure 10:
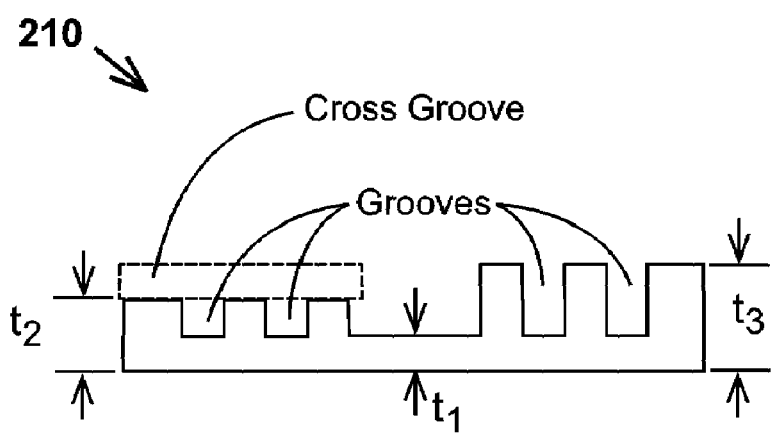
FIG. 10 is a cross-sectional view of the second exemplary spatial modulator shown in FIG. 9, as taken along the cross-section line shown in FIG. 9, according to inventions of the present application.

Eighth Exemplary Embodiment: Multi-Tiered Spatial Modulators. As previously mentioned, the use of a spatial modulator having regions with three different thicknesses, along with additional processing of the data, enables the values of TP(x,y) to be effectively measured and accounted for during a scan of an object, and obviates the need for a step of calibrating the spatial modulator. In addition, spatial variation in the absorption of the modulator, which can be caused by using a flat-plate spatial modulator, can be accounted for. An example of such a modulator is shown at 210 in FIGS. 9 and 10. Modulator 210 comprises a flat plate with a first plurality of deep grooves that run parallel to one another, and a plurality of shallow cross grooves that run parallel to one another and at an angle to the deep grooves at an angle. The angle can be 90 degrees, as shown in FIG. 9. The construction of the grooves results in a modulation plate having portions at three different thicknesses, which we will call thicknesses t1, t2, and t3, as shown in FIG. 10. Each of the grooves and cross-grooves preferably has smooth edges (e.g., smoothly changing). The locations between grooves are referred to as strips. The strips are preferably equally spaced from one another by a distance $d_S$, with the grooves being equally spaced from one another by the same distance. The strips preferably have the same width $w_S$, and the grooves preferably have the same width $w_G$. The cross grooves preferably have the same width $w_{CG}$, and are preferably equally spaced from one another by a distance $d_{CG}$. Modulator 210 may be formed by machining or molding. Other embodiments of spatial modulators may have apertures for one set of the portions, which would have a thickness of zero.

We begin the description of the framework for these embodiments by noting that the transmission factor "$\tau$" of radiation through a thickness "t" of material can be related to the material's absorption coefficient "$\alpha$" by the following exponential relationship: $\tau = e^{-\alpha \cdot t}$, where $\tau$ is the ratio of the radiation that exits the material to the radiation that enters the material. The absorption coefficient $\alpha$ has units of reciprocal length. In the case of zero thickness, $\tau$ would have a value of 1. We propose the following more general form for the transmission pattern function TP(x,y,r):

$$TP(x,y,r) = e^{-\alpha(x,y,r) \cdot t(x,y)} \quad [35]$$

where t(x,y) is known and has one of at least three values: t1, t2, and t3. $\alpha(x,y,r)$ is taken as an unknown that can vary over the x- and y-domains of the imaging device, and with each projection (to account for differences caused by temperature variations and radiation exposure). For flat plate modulators, $\alpha(x,y,r)$ will normally increase in value for (x,y) points lying further away from the center of the plate. This is because the radiation angle deviates further from the perpendicular direction, causing the radiation to traverse more of the material. While this effect would normally be accounted for by making the thickness values change with the x- and y-coordinates, it is easier to account for the effect in the absorption function $\alpha(x,y,r)$. Since the angle deviation proportionately affects the thickness values, it can be accounted for in $\alpha(x,y,r)$.

Equation [8'] may be rewritten as:

$$P^M_{MEAS}(x,y,r) = e^{-\alpha(x,y,r) \cdot t(x,y)} \cdot B(x,y,r) + IP(r) \cdot E_{SPACE}(x,y,r) \quad [36]$$

where $B(x,y,r) = [IP(r) \cdot Gr(x,y,r-1) \cdot Z(x,y,r)] \cdot P_{TRUE}(x,y,r) + E'_{TIME}(x,y,r)$.

At each projection r, the following three projection surfaces $P_1(x,y,r)$, $P_2(x,y,r)$, and $P_3(x,y,r)$ may be constructed using interpolation/extrapolation, as described above, with each surface using a t(x,y) value of t1, t2, or t3, respectively:

$$P_1(x,y,r) = P^M_{MEAS}(x,y,r)|_{t1} = e^{-\alpha(x,y,r) \cdot t1} \cdot B(x,y,r) + IP(r) \cdot E_{SPACE}(x,y,r) \quad [37a]$$

$$P_2(x,y,r) = P^M_{MEAS}(x,y,r)|_{t2} = e^{-\alpha(x,y,r) \cdot t2} \cdot B(x,y,r) + IP(r) \cdot E_{SPACE}(x,y,r) \quad [37b]$$

$$P_3(x,y,r) = P^M_{MEAS}(x,y,r)|_{t3} = e^{-\alpha(x,y,r) \cdot t3} \cdot B(x,y,r) + IP(r) \cdot E_{SPACE}(x,y,r). \quad [37c]$$

Equations [37] are non-linear, and can be solved for $\alpha(x,y,r)$ using Newton's method, a non-linear least-squares fitting method, or linearization approximation methods. Direct solutions for $\alpha(x,y,r)$ for specific values of thicknesses, and a good general approximation, are provided below.

Similar to previous exemplary embodiments, we estimate values for $\alpha(X_m, Y_n, r)$ on a coarse $X_m$–$Y_n$ grid of points (e.g., a coarse grid), and then generate the values for the individual detectors $(x_i, y_j)$ by interpolating/extrapolating the coarse set of values. Then, values of $TP(X_m, Y_n, r)$ are generated according to equation [35] using the values of $\alpha(X_m, Y_n, r)$ and $t(X_m, Y_n)$. To generate the coarse set of $\alpha(X_m, Y_n, r)$ values, representative values $Rep(X_m, Y_n, r)$ are generated for $P^M_{MEAS}(X_m, Y_n, r)$ on selected points in the $X_m$–$Y_n$ grid, as described above for other embodiments of the invention. A first portion of these representative values, $Rep_1(X_m, Y_n, r)$, will be for points that were radiated by radiation passing through thickness t1 of the modulator. A second portion of these representative values, $Rep_2(X_m, Y_n, r)$, will be for points that were radiated by radiation passing through thickness t2 of the modulator. And a third portion of these representative values, $Rep_3(X_m, Y_n, r)$, will be for points that were radiated by radiation through thickness t3 of the modulator. The representative values are substituted for the corresponding modulated measured values in equations [37], as follows:

$$Rep_1(X_m, Y_n, r) = e^{-\alpha(Xm,Yn,r)\cdot t1} \cdot B(X_m, Y_n, r) + IP(r) \cdot E_{SPACE}(X_m, Y_n, r) \quad [38a]$$

$$Rep_2(X_m, Y_n, r) = e^{-\alpha(Xm,Yn,r)\cdot t2} \cdot B(X_m, Y_n, r) + IP(r) \cdot E_{SPACE}(X_m, Y_n, r) \quad [38b]$$

$$Rep_3(X_m, Y_n, r) = e^{-\alpha(Xm,Yn,r)\cdot t3} \cdot B(X_m, Y_n, r) + IP(r) \cdot E_{SPACE}(X_m, Y_n, r) \quad [38c]$$

and these equations are solved for $\alpha(X_m, Y_n, r)$ on a coarse $X_m$–$Y_n$ grid of points. A good general approximation for the solution to equations [38] for t1<t2<t3 is:

$$\alpha(X_m, Y_n, r) = \frac{-\operatorname{Ln}\left[Q(X_m, Y_n, r) \cdot \left(\frac{t2-t1}{t3-t2}\right)\right]}{t2-t1}, \text{ and} \quad [39a]$$

$$TP(X_m, Y_n, r) = e^{-\alpha(Xm,Yn,r)\cdot t(Xm,Yn)} \quad [39b]$$

$$= \left[Q(X_m, Y_n, r) \cdot \left(\frac{t2-t1}{t3-t2}\right)\right]^{\left(\frac{t(Xm,Yn)}{t2-t1}\right)},$$

where $Q(X_m, Y_n, r)$ is the following ratio of representative values:

$$Q(X_m, Y_n, r) = [Rep_2(X_m, Y_n, r) - Rep_3(X_m, Y_n, r)]/[Rep_1(X_m, Y_n, r) - Rep_2(X_m, Y_n, r)] \quad [40]$$

Under the condition $t2 = 2 \cdot t1$ and $t3 = 3 \cdot t1$, the follow direct solution to equation [38] exists:

$$\alpha(X_m, Y_n, r) = -Ln[Q(X_m, Y_n, r)]/t1 \text{ and}$$

$$TP(X_m, Y_n, r) = Q(X_m, Y_n, r)^{t(Xm,Yn)/t1}. \quad [41]$$

With $\alpha(X_m, Y_n, r)$ estimated by equations [39] or [41], or by a solution of the non-linear equations [38], it may be inserted into equations [38] as a known value, which then makes equations [38] linear. From the linearlized equations [38], $E_{SPACE}(X_m, Y_n, r)$ may be estimated by an application of a least-squares method to the linearlized equations. Also, any two of the three linearlized equations [38] may be combined to solve for $E_{SPACE}(X,Y,r)$, such as:

$$E_{SPACE}(X_m, Y_n, r) = \frac{Rep_1(X_m, Y_n, r) - Rep_2(X_m, Y_n, r) \cdot e^{\alpha(Xm,Yn,r)(t2-t1)}}{IP(r) \cdot [1 - e^{\alpha(Xm,Yn,r)(t2-t1)}]} \quad [42a]$$

$$= \frac{Rep_1(X_m, Y_n, r) - Rep_2(X_m, Y_n, r) \cdot T1(X_m, Y_n, r)/T2(X_m, Y_n, r)}{IP(r) * [1 - T1(X_m, Y_n, r)/T2(X_m, Y_n, r)]}, \quad [42b]$$

where $T1(X_m, Y_n, r) = e^{-\alpha(Xm,Yn,r)\cdot t1}$ and $T2(X_m, Y_n, r) = e^{-\alpha(Xm,Yn,r)\cdot t2}$, and may be viewed as thickness functions. $E_{SPACE}(X_m, Y_n, r)$ may be viewed as the difference between the representative values of two of the projection surfaces, with one of the projection surfaces being multiplied by the ratio of the illumination intensities for the surfaces, and with the difference being divided by the difference between unity and the illumination ratio.

As can be seen from equation [42a], the end use of $\alpha(X_m, Y_n, r)$ is as a product with a thickness difference, with the product having dimensionless units since $\alpha(X_m, Y_n, r)$ has units of reciprocal length. This means that when one only needs to use this product and one does not need to know the exact value of $\alpha(X_m, Y_n, r)$, one can use relative values for the thicknesses rather than the actual values. Specifically, when using relative thickness values for t1, t2, and t3, each of equations [39] and [41] divides its logarithmic term by a relative thickness value to generate $\alpha(X_m, Y_n, r)$, and in turn $\alpha(X_m, Y_n, r)$ is multiplied by a relative thickness value to generate the product, and thus the offset from the absolute thickness values cancels out in the product. Thus, to use many aspects of this invention, one need only know values of the thicknesses that are representative of their relative values. These representative values can be the true known values or relative values.

In the above manner, $E_{SPACE}(X_m, Y_n, r)$ may be estimated without a need for a calibration step to determine the relative thicknesses t1, t2, and t3 of the spatial modulator. $E_{SPACE}(X_m, Y_n, r)$ may be provided to the above-described Seventh embodiment, or to other embodiments, to aid in estimating $E_{TIME}(X_m, Y_n, r)$. $E_{SPACE}(X_m, Y_n, r)$ and $E_{TIME}(X_m, Y_n, r)$ may then be interpolated/extrapolated to provide $E_{SPACE}(x_i, y_j, r)$ and $E_{TIME}(x_i, y_j, r)$ over the pixels locations, and $P_{TRUE}(x_i, y_j, r)$ may be estimated.

Method, Computer-Program Product, and System Implementations of all Embodiments, including the Seventh and Eighth Exemplary Embodiments. Each of the above-described methods may be implemented by computer program products that direct a computer system to perform the actions of the methods. Each such computer program product may comprise sets of instructions embodied on a tangible computer-readable medium that direct the processor of a computer system to perform the corresponding actions. Examples of such computer-readable mediums are the instruction memory shown for the controller shown in FIG. 2. The instructions may be in executable computer code (such as C, C++), human-readable code (such as MatLab Code), and the like. Other types of tangible computer-readable media include floppy disks, removable hard disks, optical storage media such as CD-ROMS, DVDs and bar codes, semiconductor memories such as flash memories, read-only-memories (ROMS), battery-backed volatile memories, networked storage devices, and the like. Given the above-detailed description of the various method embodiments of the inventions of the present application, it is within the skill of one of ordinary skill in the tomography art to implement each of the method embodiments disclosed herein in a computer program product without undue experimentation. Such computer program product may be run on the processor shown in FIG. 2, or on separate processors that are not coupled to Cone-beam Computer Tomography Systems.

Exemplary system inventions of the present application may comprise the radiation source, the imaging device, and the controller shown in FIG. 2, in combination with various computer program product inventions and/or methods of the present application.

Any recitation of "a", "an", and "the" is intended to mean one or more unless specifically indicated to the contrary.

The terms and expressions which have been employed herein are used as terms of description and not of limitation, and there is no intention in the use of such terms and expressions of excluding equivalents of the features shown and described, it being recognized that various modifications are possible within the scope of the invention claimed.

Moreover, one or more features of one or more embodiments of the invention may be combined with one or more features of other embodiments of the invention without departing from the scope of the invention.

While the present invention has been particularly described with respect to the illustrated embodiments, it will be appreciated that various alterations, modifications, adaptations, and equivalent arrangements may be made based on the present disclosure, and are intended to be within the scope of the invention and the appended claims.

What is claimed is:

1. A method of taking a radiographic projection of an object, the method comprising:
   disposing an object between a radiation source and an imaging device, with a spatial modulator being disposed between the radiation source and the object, the spatial modulator comprising a body of material, a plurality of first regions in the body that have thicknesses that are equal to or less than a first thickness value, and a plurality of second regions in the body that have thicknesses that are greater than the first thickness value, wherein a plurality of first regions are disposed along a geometry line with one or more of the second regions being disposed between said plurality of the first regions, wherein at least one of the first regions has transmission factor T1 for radiation passing through the at least one of the first regions, wherein a second region adjacent to said at least one of the first regions has a second transmission factor T2 for radiation passing through said second region, and wherein the ratio of the second transmission factor T2 to the first transmission factor T1 is in the range of 0.85 to 0.97; and
   exposing the object to radiation from the radiation source so that radiation passing through a plurality of first regions and a plurality of second regions of the spatial modulator strikes the object at the same time.

2. The method of claim 1 wherein the spatial modulator further comprises a plurality of third regions in the body of material that have thicknesses that are equal to or greater than a second thickness value, wherein the second thickness value is greater than the first thickness value, and
   wherein the thicknesses of the second regions are less than the second thickness value.

3. The method of claim 2 wherein a plurality of third regions are disposed along a geometry line, and wherein a plurality of regions having thicknesses less than the second thickness value are disposed between said plurality of the third regions.

4. The method of claim 1 wherein exposing the object to radiation from the radiation source comprises exposing the object to a first level of radiation intensity from the radiation source to generate a first radiographic projection, and exposing the object to a second level of radiation intensity from the radiation source to generate a second radiographic projection, wherein the second level is different from the first level.

5. The method of claim 1 wherein exposing the object to radiation from the radiation source further comprises exposing the object to a third level of radiation intensity from the radiation source to generate a third radiographic projection, wherein the third level is different from the first level and different from the second level.

6. The method of claim 1, further comprising:
   reading the imaging device to obtain the radiographic projection; and
   generating from the obtained radiographic projection an estimate of a spatial error in the obtained radiographic projection.

7. A radiographic imaging system for imaging an object, the system comprising:
   a radiation source;
   an imaging device disposed opposite the radiation source and spaced therefrom to provide a space for an object to be imaged; and
   a spatial modulator disposed between the source of radiation and the imaging device, the spatial modulator being disposed closer to the radiation source than the imaging device, the spatial modulator comprising a body of material, a plurality of first regions in the body that have thicknesses that are equal to or less than a first thickness value, and a plurality of second regions in the body that have thicknesses that are greater than the first thickness value, wherein a plurality of first regions are disposed along a geometry line with one or more of the second regions being disposed between said plurality of the first regions, wherein at least one of the first regions has transmission factor T1 for radiation passing through the at least one of the first regions, wherein a second region adjacent to said at least one of the first regions has a second transmission factor T2 for radiation passing through said second region, and wherein the ratio of the second transmission factor T2 to the first transmission factor T1 is in the range of 0.85 to 0.97, the spatial modulator being further disposed so that radiation from the radiation source can pass through a plurality of first regions and a plurality of second regions of the spatial modulator at the same time and reach the imaging device.

8. The system of claim 7 wherein the spatial modulator further comprises a plurality of third regions in the body of material that have thicknesses that are equal to or greater than a second thickness value, wherein the second thickness value is greater than the first thickness value; and
   wherein the thicknesses of the second regions are less than the second thickness value.

9. The system of claim 8 wherein a plurality of third regions are disposed along a geometry line, and wherein a plurality of regions having thicknesses less than the second thickness value are disposed between said plurality of the third regions.

10. The system of claim 7 further comprising a controller that reads the imaging device, generates radiographic projections from the data read from the imaging device, and controls the radiation intensity of the radiation source, wherein the controller exposes the object to a first level of radiation intensity from the radiation source to generate a first radiographic projection, and exposes the object to a second level of radiation intensity from the radiation source to generate a second radiographic projection, wherein the second level is different from the first level.

11. The system of Claim 10 wherein the controller exposes the object to a third level of radiation intensity from the radiation source to generate a third radiographic projection, wherein the third level is different from the first level and different from the second level.

12. A spatial modulator adapted for use in a radiographic imaging system having a radiation source and an imaging device disposed opposite to the radiation source, the imaging device having an imaging area, the spatial modulator comprising:
- a body of material having an area that is less than the imaging area of the imaging device;
- a plurality of first regions in the body that have thicknesses that are equal to or less than a first thickness value; and
- a plurality of second regions in the body that have thicknesses that are greater than the first thickness value;
- wherein a plurality of first regions are disposed along a geometry line with a plurality of second regions being disposed between said plurality of the first regions in an interleaved manner; and
- wherein at least one of the first regions has transmission factor T1 for radiation passing through the at least one of the first regions, wherein a second region adjacent to said at least one of the first regions has a second transmission factor T2 for radiation passing through said second region, and wherein the ratio of the second transmission factor T2 to the first transmission factor T1 is in the range of 0.85 to 0.97.

13. The spatial modulator of claim 12 further comprising a plurality of third regions in the body of material that have thicknesses that are equal to or greater than a second thickness value; and
- wherein the second thickness value is greater than the first thickness value, and wherein the thicknesses of the second regions are less than the second thickness value.

14. The spatial modulator of claim 13 wherein a plurality of third regions are disposed along a geometry line, and wherein a plurality of regions having thicknesses less than the second thickness value are disposed between said plurality of the third regions.

* * * * *